(12) United States Patent
Koivunen et al.

(10) Patent No.: US 7,205,383 B2
(45) Date of Patent: Apr. 17, 2007

(54) PEPTIDE LIGANDS OF LEUKOCYTE INTEGRINS

(75) Inventors: Erkki Koivunen, Helsinki (FI); Carl G. Gahmberg, Helsinki (FI)

(73) Assignee: Karyon-CTT Ltd., Helsinki (FI)

( * ) Notice: Subject to any disclaimer, the term of this patent is extended or adjusted under 35 U.S.C. 154(b) by 213 days.

(21) Appl. No.: 10/469,131

(22) PCT Filed: Mar. 11, 2002

(86) PCT No.: PCT/FI02/00188

§ 371 (c)(1),
(2), (4) Date: Aug. 27, 2003

(87) PCT Pub. No.: WO02/072618

PCT Pub. Date: Sep. 19, 2002

(65) Prior Publication Data

US 2004/0259798 A1    Dec. 23, 2004

(30) Foreign Application Priority Data

Mar. 12, 2001   (FI) .................................. 20010491

(51) Int. Cl.
*A61K 38/12* (2006.01)
(52) U.S. Cl. ..................................... 530/317
(58) Field of Classification Search .................. 514/15
See application file for complete search history.

(56) References Cited

U.S. PATENT DOCUMENTS

| | | | |
|---|---|---|---|
| 5,362,831 A * | 11/1994 | Mongelli et al. | 526/304 |
| 5,821,329 A | 10/1998 | Lobl et al. | |
| 5,840,485 A * | 11/1998 | Lebl et al. | 435/6 |
| 5,877,275 A | 3/1999 | Arnaout | |

OTHER PUBLICATIONS

Cutting S.M et al, "Sporulation operon spoIVF and the characterization of mutations that uncouple mother-cell from the forespore gene expression in *Bacillus subtillis*," J. Mol. Biol. 221:1237-1256(1991).*
Erkki Koivunen et al, "Inhibition of B2 Integrin-mediated Leukocyte Cell Adhesion by Leucine—Leucine-Glycine Motif-containing Peptides," The Journal of Cell Biology, vol. 153, No. S, May 28, 2001.*
Gura, "Systems for Identifying New Drugs Are Often Faulty" Science (1997), vol. 278, pp. 1041 and 1042.*
Ishibashi, Norio et al, "Studies on flavored peptides. Part I. Bitterness of leucine-containing peptides," Agricultural and Biological Chemistry (1987), 51(9), 2389-94.*
Erkki Koivunen, The Journal of Cell Biology, vol. 153, No. 5, May 28, 2001, pp. 905-915.
Koivunen et al.: Phage Libraries Displaying Cyclic Peptides with Different Ring Sizes: Ligand Specificities of the RGD- Directed Integrins, BIO/TECHNOLOGY, vol. 13, Mar. 1995, pp. 265-270.
Ross et al.: Inhibition of Molt-4-Endothelial Adherence by Synthetic Peptides from the Sequence of ICAM-1, The Journal of Biological Chemistry, vol. 267, No. 12, pp. 8537-8543, 1992.

* cited by examiner

*Primary Examiner*—Cecilia J. Tsang
*Assistant Examiner*—Thomas S. Heard
(74) *Attorney, Agent, or Firm*—Birch, Stewart, Kolasch & Birch, LLP

(57) ABSTRACT

The present invention relates to novel peptides which are useful as antagonists of the $\beta_2$ integrins, to pharmaceutical compositions comprising these peptides, to the use of the novel peptides for the manufacture of pharmaceutical compositions for the treatment of inflammatory diseases and human leukemias and for inhibiting leukocyte cell adhesion and migration in general, to a method for therapeutic or prophylactic treatment of inflammatory diseases and human leukemias and to the use of the novel peptides as $\beta_2$ integrin antagonists for biochemical isolation and purification procedures in vitro.

8 Claims, 13 Drawing Sheets

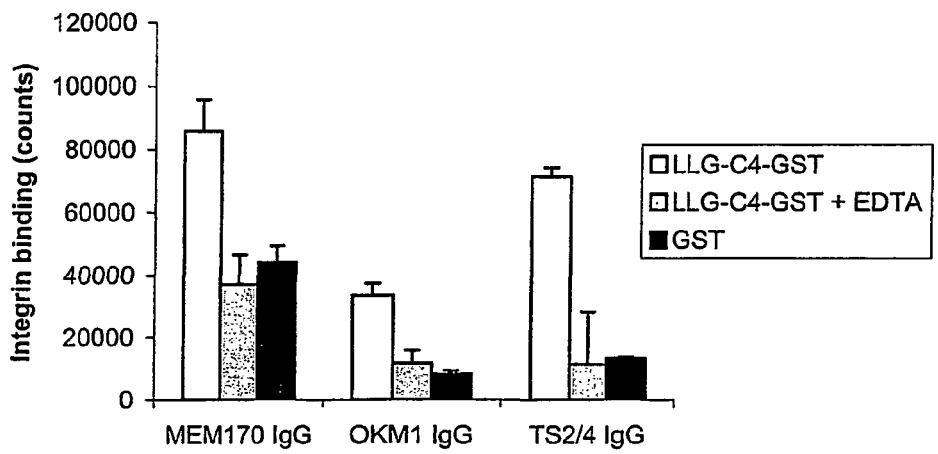
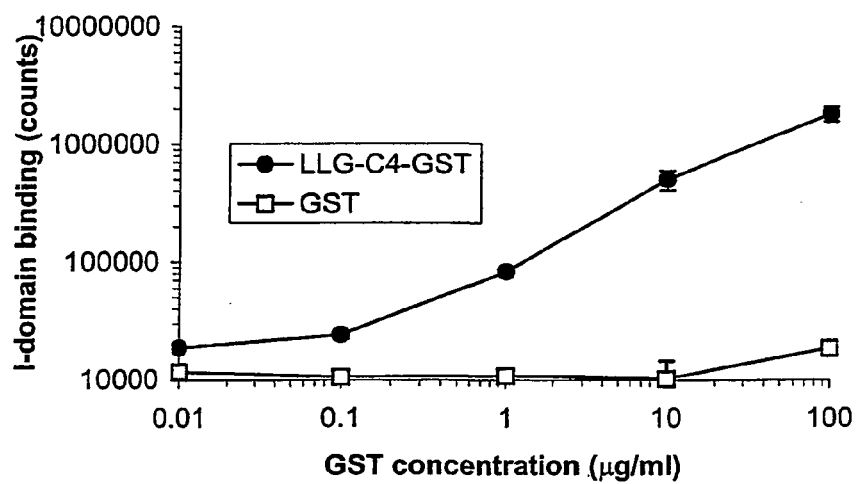
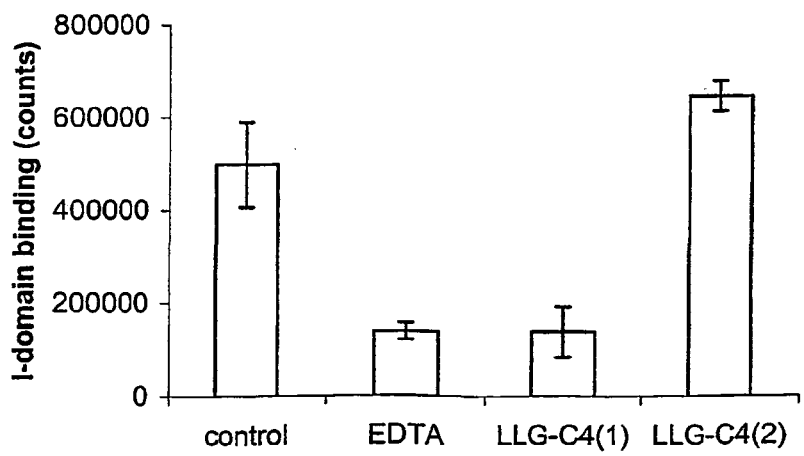
Fig. 1

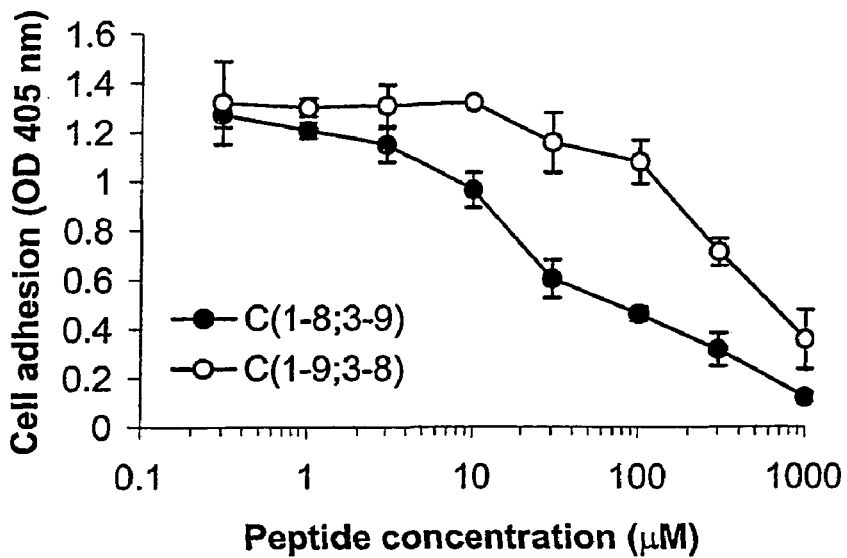
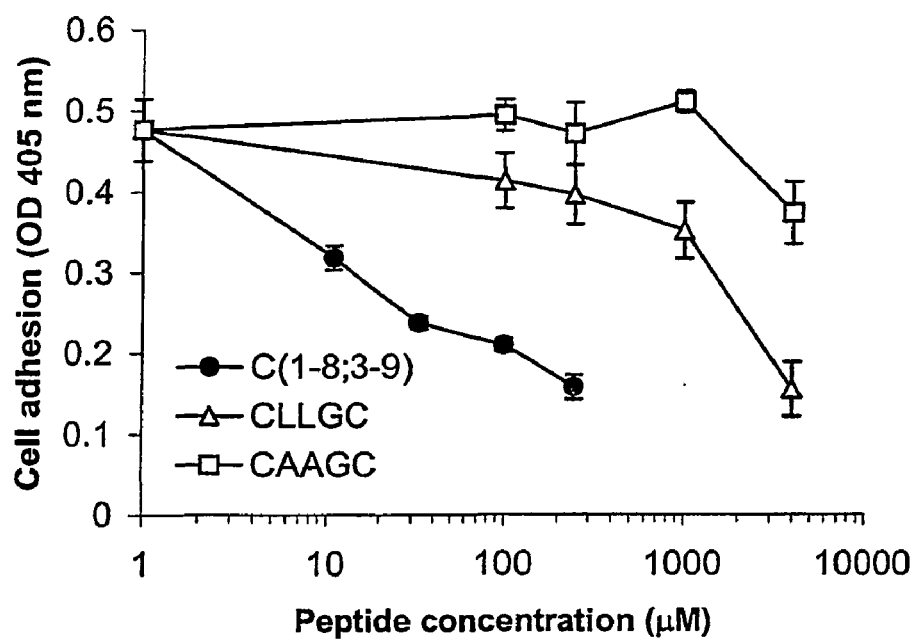
Fig. 3

A
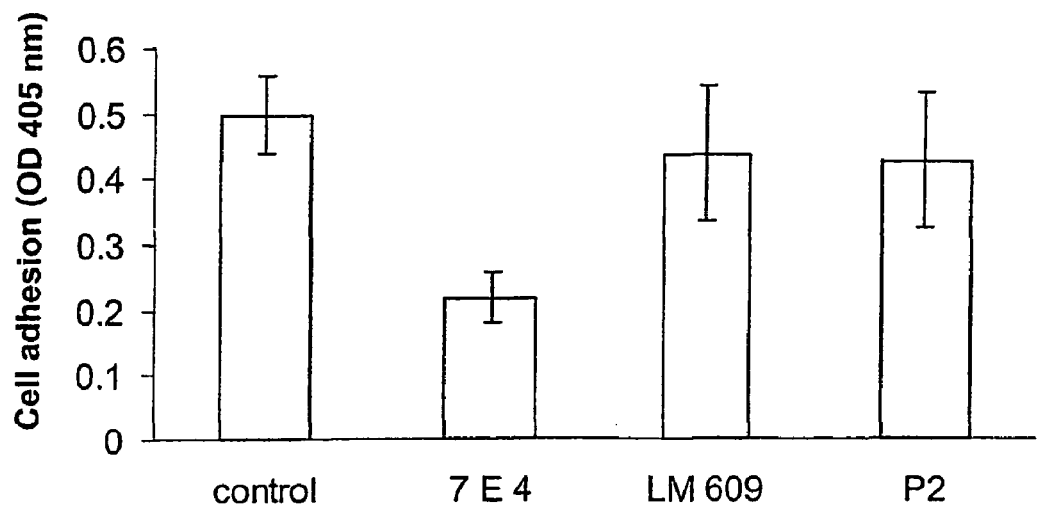
B
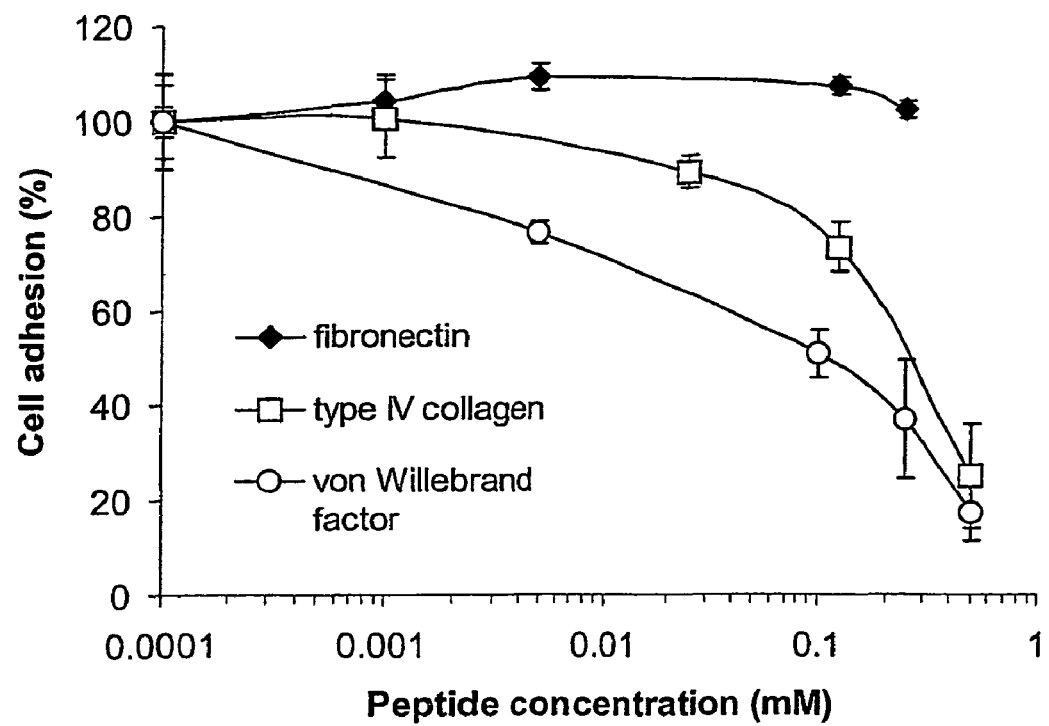
Fig. 5

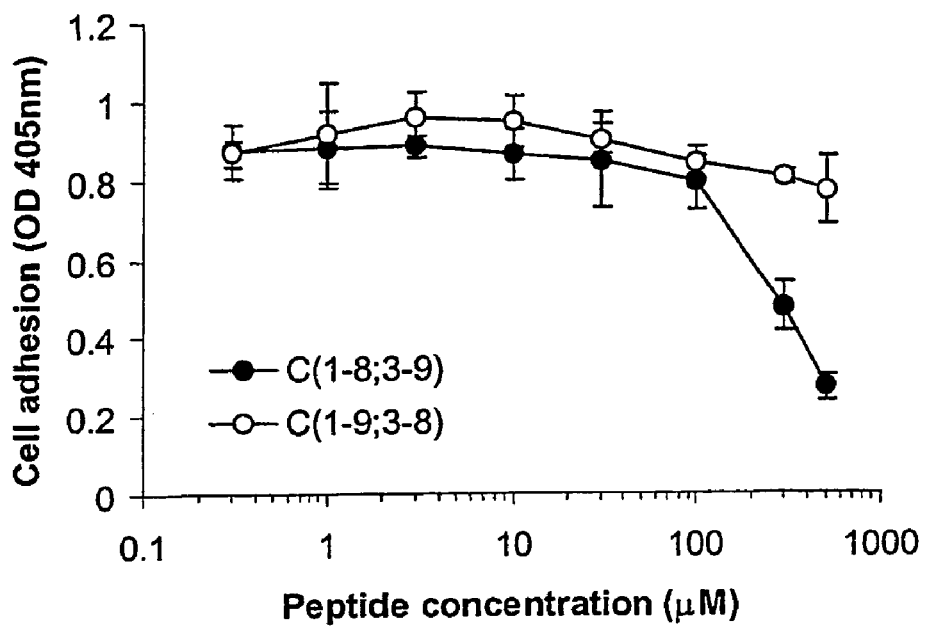
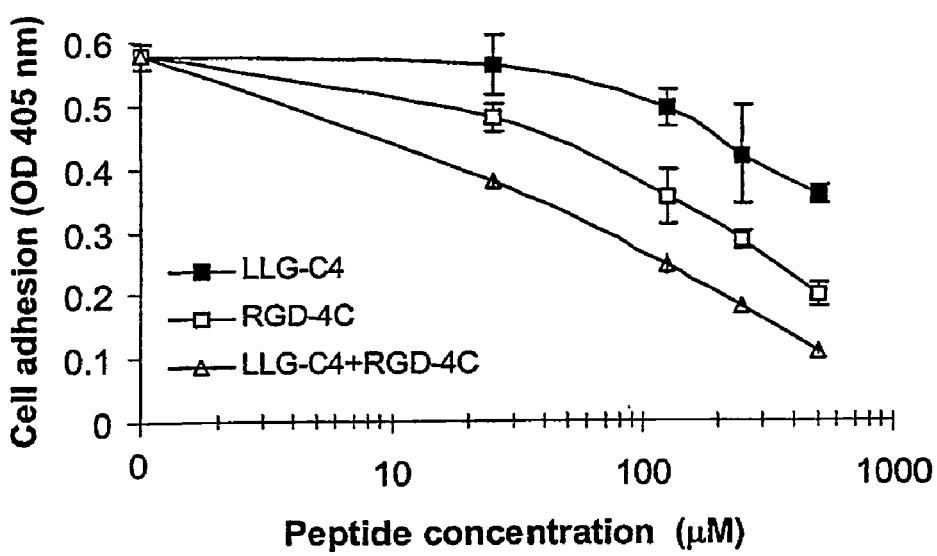
Fig. 6 A, B

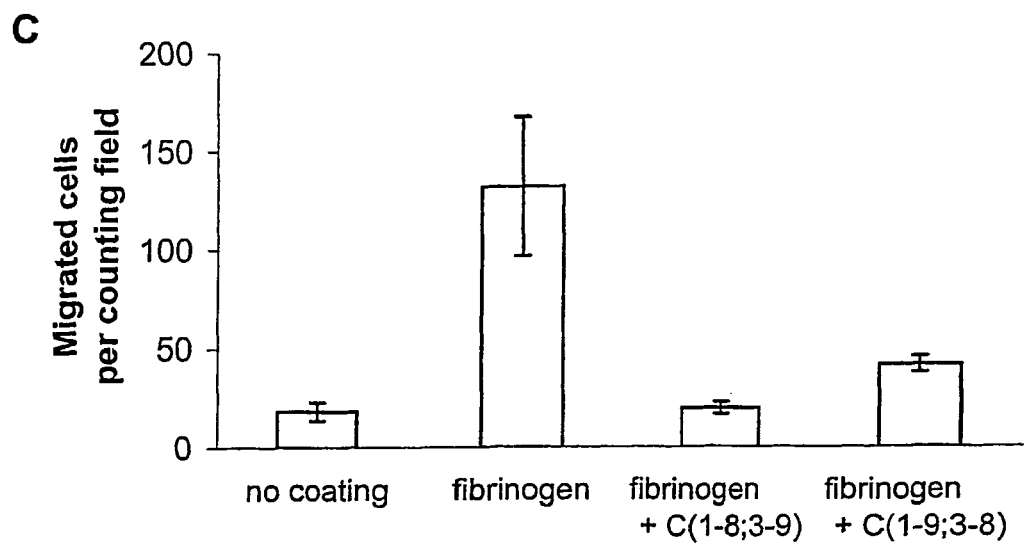
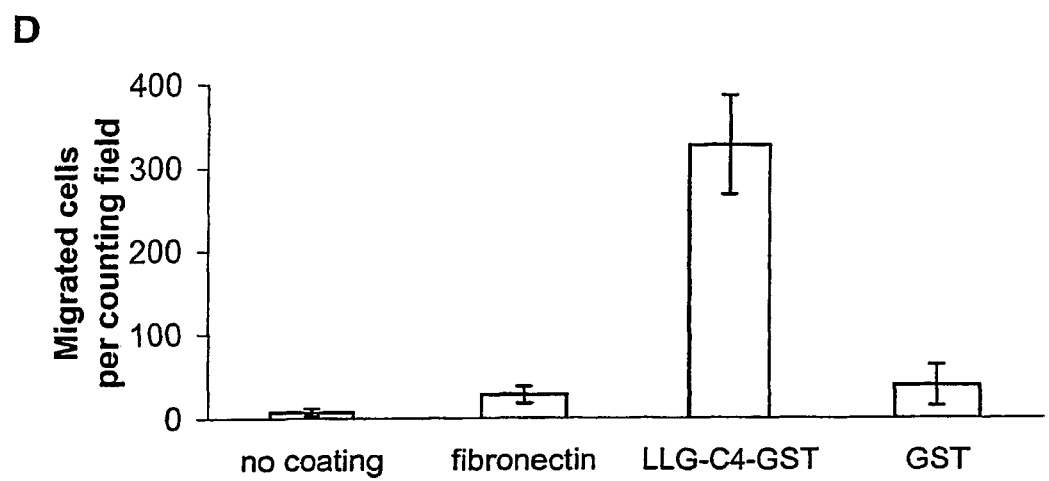
Fig. 6 C, D

SEQUENCE LISTING

<160> NUMBER OF SEQ ID NOS: 27

<210> SEQ ID NO 1
<211> LENGTH: 3

```
<212> TYPE: PRT
<213> ORGANISM: Unknown
<220> FEATURE:
<223> OTHER INFORMATION: Peptide of the claimed invention

<400> SEQUENCE: 1

Leu Leu Gly
1

<210> SEQ ID NO 2
<211> LENGTH: 9
<212> TYPE: PRT
<213> ORGANISM: Unknown
<220> FEATURE:
<223> OTHER INFORMATION: Peptide of the claimed invention
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 2

Cys Xaa Cys Xaa Leu Leu Gly Cys Cys
1               5

<210> SEQ ID NO 3
<211> LENGTH: 9
<212> TYPE: PRT
<213> ORGANISM: Unknown
<220> FEATURE:
<223> OTHER INFORMATION: LLG-C4 peptide of the claimed invention

<400> SEQUENCE: 3

Cys Pro Cys Phe Leu Leu Gly Cys Cys
1               5

<210> SEQ ID NO 4
<211> LENGTH: 5
<212> TYPE: PRT
<213> ORGANISM: Unknown
<220> FEATURE:
<223> OTHER INFORMATION: Synthetic peptide seen in Fig. 3B

<400> SEQUENCE: 4

Cys Leu Leu Gly Cys
1               5

<210> SEQ ID NO 5
<211> LENGTH: 5
<212> TYPE: PRT
<213> ORGANISM: Unknown
<220> FEATURE:
<223> OTHER INFORMATION: Synthetic peptide seen in Fig. 3B

<400> SEQUENCE: 5

Cys Ala Ala Gly Cys
1               5

<210> SEQ ID NO 6
<211> LENGTH: 7
<212> TYPE: PRT
<213> ORGANISM: Unknown
<220> FEATURE:
<223> OTHER INFORMATION: Consensus sequence of ICAM-1 identified by
      phage display
<220> FEATURE:
```

```
<221> NAME/KEY: misc_feature
<222> LOCATION: (3)..(4)
<223> OTHER INFORMATION: Xaa can be any naturally occurring amino acid

<400> SEQUENCE: 6

Pro Pro Xaa Xaa Leu Leu Gly
1               5

<210> SEQ ID NO 7
<211> LENGTH: 8
<212> TYPE: PRT
<213> ORGANISM: Unknown
<220> FEATURE:
<223> OTHER INFORMATION: Sequence of collagen IV alpha chain

<400> SEQUENCE: 7

Leu Leu Gly Arg Pro Gly Glu Ala
1               5

<210> SEQ ID NO 8
<211> LENGTH: 6
<212> TYPE: PRT
<213> ORGANISM: Unknown
<220> FEATURE:
<223> OTHER INFORMATION: Motif which binds to alpha2beta1 integrin
<220> FEATURE:
<221> NAME/KEY: misc
<222> LOCATION: (3)..(3)
<223> OTHER INFORMATION: Xaa is hydroxyproline

<400> SEQUENCE: 8

Gly Phe Xaa Gly Glu Arg
1               5

<210> SEQ ID NO 9
<211> LENGTH: 43
<212> TYPE: DNA
<213> ORGANISM: Unknown
<220> FEATURE:
<223> OTHER INFORMATION: Forward primer used in direct colony sequencing

<400> SEQUENCE: 9
taatacgact cactataggg caagctgata aaccgataca att                    43

<210> SEQ ID NO 10
<211> LENGTH: 23
<212> TYPE: DNA
<213> ORGANISM: Unknown
<220> FEATURE:
<223> OTHER INFORMATION: Reverse primer used in direct colony sequencing

<400> SEQUENCE: 10
cctcatagtt agcgtaacga tct                                         23

<210> SEQ ID NO 11
<211> LENGTH: 11
<212> TYPE: PRT
<213> ORGANISM: Unknown
<220> FEATURE:
<223> OTHER INFORMATION: Stronly enriched sequence

<400> SEQUENCE: 11

Cys Trp Lys Leu Leu Gly Ser Glu Glu Glu Cys
1               5                   10

<210> SEQ ID NO 12
<211> LENGTH: 9
```

```
<212> TYPE: PRT
<213> ORGANISM: Unknown
<220> FEATURE:
<223> OTHER INFORMATION: Phage sequence bound to the alphaMbeta2
      integrin (Mac-1)

<400> SEQUENCE: 12

Cys Trp His Lys Asp Leu Leu Gly Cys
1               5

<210> SEQ ID NO 13
<211> LENGTH: 9
<212> TYPE: PRT
<213> ORGANISM: Unknown
<220> FEATURE:
<223> OTHER INFORMATION: Phage sequence bound to the alphaMbeta2
      integrin (Mac-1)

<400> SEQUENCE: 13

Cys Trp Ser Met Glu Leu Leu Gly Cys
1               5

<210> SEQ ID NO 14
<211> LENGTH: 9
<212> TYPE: PRT
<213> ORGANISM: Unknown
<220> FEATURE:
<223> OTHER INFORMATION: Phage sequence bound to the alphaMbeta2
      integrin (Mac-1)

<400> SEQUENCE: 14

Cys Pro Pro Asp Leu Phe Trp Tyr Cys
1               5

<210> SEQ ID NO 15
<211> LENGTH: 9
<212> TYPE: PRT
<213> ORGANISM: Unknown
<220> FEATURE:
<223> OTHER INFORMATION: Phage sequence bound to the alphaMbeta2
      integrin (Mac-1)

<400> SEQUENCE: 15

Cys Pro Glu Asp Leu Tyr Phe Phe Cys
1               5

<210> SEQ ID NO 16
<211> LENGTH: 9
<212> TYPE: PRT
<213> ORGANISM: Unknown
<220> FEATURE:
<223> OTHER INFORMATION: Phage sequence bound to the alphaMbeta2
      integrin (Mac-1)

<400> SEQUENCE: 16

Cys Pro Glu Asp Phe Ile Phe Phe Cys
1               5

<210> SEQ ID NO 17
<211> LENGTH: 13
<212> TYPE: PRT
<213> ORGANISM: Unknown
<220> FEATURE:
<223> OTHER INFORMATION: ICAM-1

<400> SEQUENCE: 17

Cys Asp Gln Pro Lys Leu Leu Gly Ile Glu Thr Pro Leu
1               5                   10
```

```
<210> SEQ ID NO 18
<211> LENGTH: 13
<212> TYPE: PRT
<213> ORGANISM: Unknown
<220> FEATURE:
<223> OTHER INFORMATION: von Willebrand Factor-A2

<400> SEQUENCE: 18

Thr Val Gly Pro Gly Leu Leu Gly Val Ser Thr Leu Gly
 1               5                  10

<210> SEQ ID NO 19
<211> LENGTH: 13
<212> TYPE: PRT
<213> ORGANISM: Unknown
<220> FEATURE:
<223> OTHER INFORMATION: von Willebrand Factor-D3

<400> SEQUENCE: 19

Gly Arg Tyr Ile Ile Leu Leu Gly Lys Ala Leu Ser Val
 1               5                  10

<210> SEQ ID NO 20
<211> LENGTH: 13
<212> TYPE: PRT
<213> ORGANISM: Unknown
<220> FEATURE:
<223> OTHER INFORMATION: Type I collagen-alpha2

<400> SEQUENCE: 20

Pro Gly Pro Gln Gly Leu Leu Gly Ala Pro Gly Ile Leu
 1               5                  10

<210> SEQ ID NO 21
<211> LENGTH: 13
<212> TYPE: PRT
<213> ORGANISM: Unknown
<220> FEATURE:
<223> OTHER INFORMATION: Type IV collagen-alpha4

<400> SEQUENCE: 21

Pro Gly Pro Pro Gly Leu Leu Gly Arg Pro Gly Glu Ala
 1               5                  10

<210> SEQ ID NO 22
<211> LENGTH: 13
<212> TYPE: PRT
<213> ORGANISM: Unknown
<220> FEATURE:
<223> OTHER INFORMATION: Osteopontin

<400> SEQUENCE: 22

Val Ile Cys Phe Cys Leu Leu Gly Ile Thr Cys Ala Ile
 1               5                  10

<210> SEQ ID NO 23
<211> LENGTH: 29
<212> TYPE: DNA
<213> ORGANISM: Unknown
<220> FEATURE:
<223> OTHER INFORMATION: Primer containing a BamH I site

<400> SEQUENCE: 23
aggctcgagg atcctcggcc gacggggct                              29
```

```
<210> SEQ ID NO 24
<211> LENGTH: 27
<212> TYPE: DNA
<213> ORGANISM: Unknown
<220> FEATURE:
<223> OTHER INFORMATION: Primer containing a EcoR I site

<400> SEQUENCE: 24
aggtctagaa ttcgccccag cggcccc                              27

<210> SEQ ID NO 25
<211> LENGTH: 8
<212> TYPE: PRT
<213> ORGANISM: Unknown
<220> FEATURE:
<223> OTHER INFORMATION: Peptide bound to GST

<400> SEQUENCE: 25

Cys Leu Arg Ser Gly Arg Gly Cys
1               5

<210> SEQ ID NO 26
<211> LENGTH: 8
<212> TYPE: PRT
<213> ORGANISM: Unknown
<220> FEATURE:
<223> OTHER INFORMATION: Peptide bound to GST

<400> SEQUENCE: 26

Cys Pro Pro Trp Trp Ser Gln Cys
1               5

<210> SEQ ID NO 27
<211> LENGTH: 11
<212> TYPE: PRT
<213> ORGANISM: Unknown
<220> FEATURE:
<223> OTHER INFORMATION: RGD-4C peptide

<400> SEQUENCE: 27

Ala Cys Asp Cys Arg Gly Asp Cys Phe Cys Gly
1               5                   10
```

PEPTIDE LIGANDS OF LEUKOCYTE INTEGRINS

This application is the national phase under 35 U.S.C. 371 of PCT International Application No. PCT/FI02/00188 which has an International filing date of Mar. 11, 2002, which designated the United States of America.

FIELD OF THE INVENTION

The present invention relates to novel peptides which are useful as antagonists of the $\beta_2$ integrins, to pharmaceutical compositions comprising these peptides, to the use of the novel peptides for the manufacture of pharmaceutical compositions for the treatment of inflammatory diseases and human leukemias and for inhibiting leukocyte cell adhesion and migration in general, to a method for therapeutic or prophylactic treatment of inflammatory diseases and human leukemias and to the use of the novel peptides as $\beta_2$ integrin antagonists for biochemical isolation and purification procedures in vitro.

BACKGROUND OF THE INVENTION

The migration of leukocytes through the body and the various lymphoid organs is an essential element of the immune system. While circulating in blood or lymphatic vessels, leukocytes are in a resting and low adhesive state. However, when leukocytes are stimulated by signals from the immune system such as exposure to an immune complex or a chemokine gradient, their integrin adhesion receptors become activated. The activation of the integrins is essential for the many functions of leukocytes. Such functions are, for example, binding to antigen-presenting cells, recirculation through lymph nodes and migration out of the vasculature and through the extracellular matrix to sites of inflammation. The integrin activation needs to be tightly regulated as inappropriate leukocyte adhesion leads to significant injury of normal tissues.

Leukocytes express a specific subset of the integrin family, the $\beta_2$ integrins of which four members are currently known. They have a common $\beta_2$ chain (CD 18) but different $\alpha$ subunits ($\alpha_L$ or CD11a, $\alpha_M$ or CD11b, $\alpha_X$ or CD11c, and $\alpha_D$ or CD11d) (Gahmberg et al., 1997). The $\alpha$ subunits contain a conserved 200-residue A or I domain, which is essential for binding of most ligands. The crystal structures of I domains from the $\alpha_L$ and $\alpha_M$ subunits indicate the presence of a cation binding site called the metal-dependent adhesion site. Amino acid substitutions in this site abrogate ligand binding (Huang and Springer, 1995; Kamata et al., 1995).

The major ligands of these integrins, the ICAMs, belong to the immunoglobulin superfamily, and five ICAMs with slightly different binding specificities have been described. The expression of ICAM-1 on endothelial cells is subject to stimulation by inflammatory cytokines, which enhances the $\beta_2$ integrin-mediated adhesion of leukocytes on endothelial cells. In addition to the ICAMs, fibrinogen and the iC3b complement protein are known ligands of the $\beta_2$ integrins, particularly of $\alpha_M\beta_2$ (Mac-1).

Because of the importance of the N integrins for leukocyte function, antagonists of them are potential anti-inflammatory agents. Antibodies to the $\beta_2$ integrins or the ICAMs have a therapeutic effect in animal models of immunological disorders.

Agents targeting the $\beta_2$ integrins could also be valuable in the development of therapeutic strategies to human leukemias (Calancette et al., 2000). However, only a few small molecule antagonists of the 62 integrins have been described so far (Kalen et al., 1999; Kelly et al., 1999). Lack of such compounds has prevented the detailed examination of the role of each member of the $\beta_2$ integrin family in leukemia dissemination as well in inflammatory diseases. In particular, it would be desirable to design compounds that distinguish between the inactive and active state of an integrin. Modeling of such small molecule inhibitors has been hampered by the large size of the peptide ligands developed so far. Linear peptides are often without a well-defined structure when free in solution. Among the few $\beta_2$ integrin ligands discovered is the 22-amino acid long peptide known as P1 which was derived from ICAM-2 (Li et al., 1993). This peptide retains the leukocyte integrin-activating effect that is typical for ICAM-2 (Li et al., 1995; Kotovuori et al, 1999). Complementary-determining regions of anti-$\beta_2$ integrin antibodies have been another source to obtain ligand peptides, and one of the isolated peptides, 23 amino acids in length, showed similarity to a sequence present on ICAM-1 (Feng et al., 1998).

To develop smaller peptide ligand leads to the $\beta_2$ interns, the inventors screened random peptide libraries displayed on filamentous phage. The phage display technique has previously yielded selective peptide ligands to the integrin species $\alpha_5\beta_1$ (Koivunen et al., 1994), $\alpha_v\beta_3/\beta_5$(Koivunen et al., 1995) and $\alpha_v\beta_6$ (Kraft et al., 1999). Phage library screenings have also confirmed the earlier findings that the tripeptide sequence RGD is a common recognition sequence of a subset of integrins (Pierschbacher and Ruoslahti, 1984). In addition, apparent charged analogues of RGD, such as RLD, KGD, and NGR, have been discovered. The leukocyte integrins $\alpha_4\beta_1$, and $\alpha_4\beta_7$ are known to have a specificity for peptides containing another type of tripeptide sequence, LDV (Komoriya et al., 1991).

SUMMARY OF THE INVENTION

The present inventors have now found that the leukocyte-specific $\beta_2$ integrins recognize a motif comprising three amino acids. The tripeptide favored by the $\alpha_M\beta_2$ integrin turned out to be a previously unknown adhesion motif LLG. An LLG-motif is present on ICAM-1, the major $\beta_2$ integrin ligand, but also on several matrix proteins including von Wirebrand factor and collagens. The inventors developed a novel $\beta_2$ integrin antagonist peptide termed LLG-C4, which has a compact disulfide-restrained structure as determined by NMRE Especially this bicyclic peptide is a potent inhibitor of leukocyte cell adhesion and migration, and is a novel lead compound for the development of anti-inflammatory agents.

It is therefore an object of the present invention to provide novel peptides comprising the structure

LLG or a structural or chemical analogue thereof, which structure corresponds to the sequence shown in SEQ ID No. 1 of the sequence listing.

It is another object of the present invention to provide novel peptides comprising the structure

CXCXLLGCC which corresponds to the sequence shown in SEQ ID No. 2 of the sequence listing and wherein X is any amino acid residue, or a structural or chemical analogue thereof A further object of the present invention are peptides comprising the structure

CPCFLLGCC which corresponds to the sequence shown in SEQ ID No. 3 of the sequence listing, or a structural or chemical analogue thereof.

The peptides of SEQ ID No. 3 wherein the peptide is structurally constrained by two disulfide bonds are preferred. Especially preferred is the peptide with one disulfide bond between the C1 and C8 cysteines, and a second disulfide bond between the C3 and C9 cysteines.

The present invention also relates to the use of the novel peptides as pharmaceuticals. Pharmaceutical compositions comprising the novel peptides in association with a pharmaceutically acceptable carrier form also an object of the present invention.

The present invention also includes the use of the novel peptides for the manufacture of pharmaceutical compositions for the treatment of inflamatory diseases and human leukemias, and for inhibiting leukocyte cell adhesion and migration in general. A further object of the invention is a method for the therapeutic or prophylactic treatment of inflammatory diseases and human leukemias which method comprises administering a therapeutically or prophylactically effective amount of a novel peptide according to the invention to a subject in need of said treatment.

The novel peptides according to the invention can also be used as $\beta_2$ integrin antagonists in biochemical isolation and purification procedures of different integrin species and different types of leukocytic cells in vitro.

The invention is herein below described in more detail referring to the accompanied drawings.

BRIEF DESCRIPTION OF THE DRAWINGS

FIG. 1 shows how the binding of LLG-C4-GST nonapeptide to $\beta_2$ leukocyte integrin and its I-domain is divalent cation-dependent In FIG. 1(A), integrin from a blood cell lysate was immunocaptured on microtiter wells using the $\alpha_M$ subunit antibody MEM170 or OKM1 or the $\alpha_X$ subunit antibody TS2/4. Purified LLG-C4-GST or GST control (2 µg/well) was allowed to bind for 60 min in the absence or presence of EDTA. After washing, the bound GST protein was determined by using anti-GST antibodies. The results show the means ±SD from triplicate wells. The experiment was repeated three times with similar results.

In FIG. 1(B), LLG-C4-GST or GST was incubated for 60 min in microtiter wells coated with purified $\alpha_M$ subunit I-domain. The concentrations of GST proteins were as indicated. After washing, the bound GST was determined with anti-GST antibodies. The results are means ±SD from triplicate wells. The results were similar in two other experiments.

In FIG. 1(C), LLG-C4-GST (10 µg/ml) was incubated in I-domain-coated wells in the absence or presence of EDTA (2.5 mM) or the LLG-C4(1) peptide (100 µM) or the inactive LLGC4(2) peptide (100 µM). After a 60 min incubation, the wells were washed and the binding was determined with anti-GST antibodies. The results are the means ±SD from triplicate wells.

FIG. 2 shows how immobilized LLG-C4 supports $\beta_2$ integrin-directed cell adhesion.

FIG. 3 shows comparison of activities of cyclic LLG peptides. In FIG. 3(A), TBP-1 cells were mixed in suspension with the peptide containing either the C(1–8;3–9) or C(1–9;3–8) disulfide. The final concentrations of the peptides are indicated. Cells were then incubated for 60 min at 37° C. in microtiter wells coated with LLG-C4-GST. After washing the wells, the bound cells were quantitated by the phosphatase assay. The results are the mean ±SD from triplicate wells. Similar results were obtained in two other experiments with triplicate wells.

In FIG. 3(B), THP-1 cell binding to LLG-C4-GST was examined in the presence of the C(1–8;3–9), CLLGC (SEQ ID NO: 4) or the CAAGC (SEQ ID NO: 5) peptide. The synthetic peptides were used at the concentrations indicated. Following a 60 min incubation the wells were washed and the bound cells were determined by the phosphatase assay. The data show the means ±SD from triplicate wells and were similar in two other experiments.

FIG. 4 shows inhibition of leukocyte cell adhesion to ICAM-1 by LLG-C4 peptide.

FIG. 5 shows how THP-1 cell adhesion on von Willebrand factor and type IV collagen is blocked by LLG-C4 peptide. In FIG. 5(A), THP-1 cell binding to von Wirebrand factor was examined in the presence of antibodies against the $\beta_2$ (7E4), $\alpha_v\beta_3$ (LM609) or $\alpha_{IIb}\beta_3$ (P2) integrins. Following a 60 min incubation in von Willebrand factor-coated wells, the bound cells were determined. The data are the mean ±SD of triplicate wells. The experiment was repeated three times.

In FIG. 5(B), TRP-1 cells were allowed to bind to microtiter wells coated with von Willebrand factor, type IV collagen, or fibronectin. The C(1–8;3–9) peptide was included as a competitor in the concentrations described. The bound cells were determined by the phosphatase assay. The data are the mean ±SD of triplicate wells and were similar in four other experiments.

FIG. 6 shows that the synthetic LLG-C4 peptide prevents adhesion and migration of THP-1 cells on fibrinogen substratum In FIG. 6(A), THP-1 cells were administered together with the C(1–8;3–9) or C(1–9;3–8), or in the absence of peptides, in microtiter wells coated with fibrinogen. Following a 60 min incubation the bound cells were determined by the phosphatase assay. The results are the mean ±SD of triplicate wells and were similar in two other experiments.

In FIG. 6(B), to activate integrins, THP-1 cells were stimulated both with phorbol ester (50 nM) and the RGD-4C and C(1–8;3–9) peptides (each 2.5 µM for 1 h. After washing the cells were allowed to bind to fibrinogen-coated wells in the presence of C(1–8;3–9) or RGD-4C or both peptides at the concentrations indicated. After a 30-min incubation the bound cells were determined. The results are the mean ±SD of triplicate wells and were similar in two other experiments. At some data points the SD values are too small to be seen.

In FIG. 6(C), Transwell filters were coated both on the upper and lower surface with fibrinogen, or left uncoated, and then saturated with BSA. TBP-1 cells ($5 \times 10^4$ per filter) were plated on the upper surface of the filter in 10% serum-containing medium. The concentrations of C(1–8; 3–9) and C(1–9;3–8) were 200 µM. Following a 18 hour-culture, the cells migrated underneath the filter were determined. The cells were fixed, stained, and then counted under a microscope. The results show means ±SD of at least three experiments.

In FIG. 6(D), both sides of the Transwell filters were coated with LLG-C4-GST, GST, fibrinogen, or BSA. A total of $5 \times 10^4$ TP-1 cells was administered per filter in 10% serum-containing medium. Cells were cultured for 18 h, and the number of cells migrated to the lower surface of filter was counted microscopically. The results show means ±SD of at least three experiments.

FIG. 7 shows comparison of structures of cyclic LLG-C4 peptide conformers by NMR.

DETAILED DESCRIPTION OF THE INVENTION

Figure 2A:
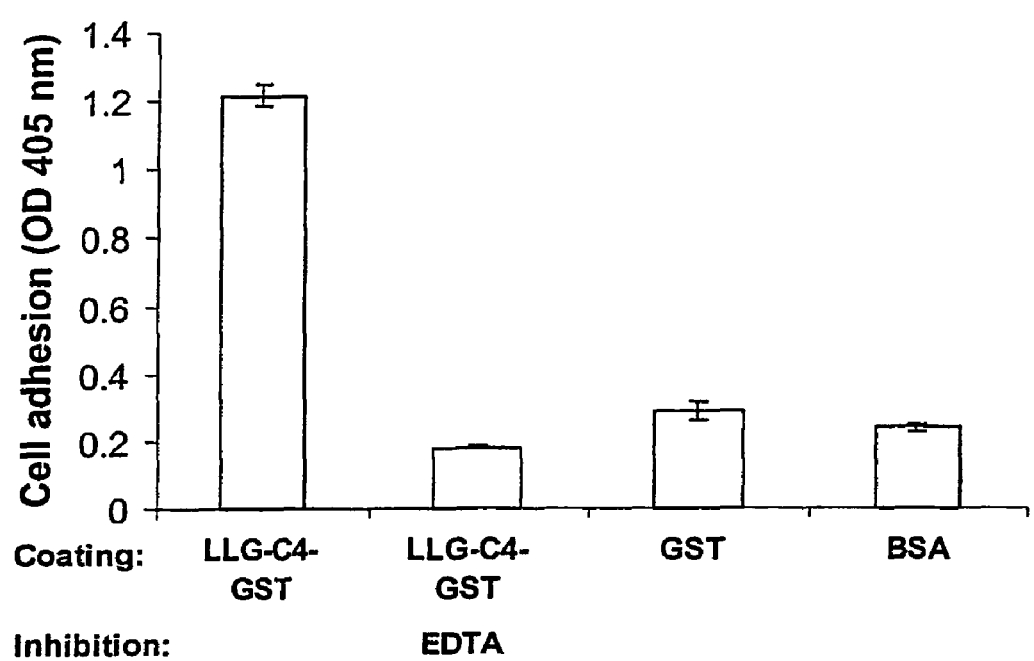
In FIG. 2(A), phorbol ester-activated THP-1 cells were allowed to bind for 60 min to microtiter wells coated with LLG-C4-GST, GST, or albumin. EDTA was included at a 2.5 mM concentration. The bound cells were determined by the assay measuring cellular phosphatase activity. The data are the means ±SD from triplicate wells. Similar results were obtained in six other experiments.

The novel highly specific peptide antagonists containing the unexpected LLG tripeptide binding motif were developed using phage display. The novel peptides inhibit leukocyte adhesion, and when immobilized, they support leukocyte adhesion. The most active antagonist CPCFLLGCC (SEQ ID NO: 3) (called LLG-C4) is a biscyclic nonapeptide that is structurally restrained by two disulfide bonds and contains a LLG tripeptide binding motif favoured by the $\beta_2$ integrins. The LLG-C4 peptide specifically blocked the $\beta_2$ integrin-mediated leukocyte adhesion and inhibited leukocyte binding to their major ligand ICAM-1. Furthermore, like a typical integrin ligand, the peptide supported cell adhesion when immobilized on plastic and bound leukocytic cell lines but not cells lacking $\beta_2$ integrins. The effectiveness and leukocyte specificity of the peptide is explained by its ability to interact with the I-domain, which is a known active site in the leukocyte integrins. Interestingly, not only ICAM-1 but a number of other adhesion proteins including von Willebrand factor and type IV collagen contain the consensus PP/XXLLG (SEQ ID NO: 6) sequence identified by phage display. Our studies show that von Willebrand factor and type IV collagen are potential ligands for the leukocyte $\beta_2$ integrins.

The activity of the most active antagonist, LLG-C4 nonapeptide, was strictly dependent on the correct formation of two disulfide bridges. There was a 20-fold difference in the activities of two biscyclic conformers that differed only in the arrangement of the disulfide bridges. The more active peptide had a very compact structure due to "crossing" arrangement of the disulfide bonds as shown by NMR. Interestingly, the leucine side chains protrude from the cyclic structure like antennas suggesting that they can directly interact with the integrin. The small glycine residue may adjust a correct distance between the two leucine side chains.

Previous studies have indicated that synthetic peptides spanning the LLG region of ICAM-1 (Ross et al., 1992) or the corresponding region of ICAM-2 (Li et al., 1993) support leukocyte adhesion when the peptides are immobilized on plastic. In soluble forms, the peptides block binding of leukocytic cells to ICAM-1 expressed on an endothelial cell monolayer. The LLG-C4 nonapeptide is significantly smaller than the previously described peptide ligands for the $\beta_2$ integrins and showed high activity though lacking a negatively charged amino acid residue such as glutamate. Also the pentapeptide CLLGC (SEQ ID NO: 4) inhibited cell adhesion Thus, $\beta_2$ integrin-targeting ligands can be constructed based on the non-charged LLG motif. This is in accordance with the crystal structures and structural models of the first Ig domain of ICAM-1 where the LLG sequence is seen as part of a short β strand apparently capable of directly contacting with an integrin I-domain (Casasnovas et al., 1998; Bella et al., 1998). Alanine scanning mutagenesis studies of individual amino acids within the first Ig domain of ICAM-1 have shown that the LLG region is important for the integrin binding of ICAM-1. Mutation of one of the leucine residues decreases ICAM-1 binding activity partially and mutation of the glycine completely (Fisher et al., 1997). Because of the inactivity of the glycine-mutated ICAM-1, it has been suggested that the glycine residue does not play a structural role but rather directly interacts with the integrin Mutations of the corresponding valine and glycine amino acids to alanines in ICAM-2 also give proteins with impaired integrin-binding activity (Casasnovas et al., 1999).

von Willebrand factor contains two LLG sequences but an ability of these sequences to interact with integrins has not been reported. von Willebrand factor is a multifunctional adhesive ligand binding several proteins and prevents bleeding during vascular injury by mediating platelet adhesion to exposed subendothelium. It contains two RGD sequences at least one of which is important in binding the platelet integrin $\alpha_{IIb}\beta_3$. According to the inventors' knowledge, there are no known mutations in the LLG sequences associated with bleeding disorders in von Willebrand's disease. The inventors found strong binding of phorbol ester-activated leukocytic cells to von Willebrand factor. The binding appeared to be predominantly mediated by the LLG motif as it was inhibited by the $\beta_2$ integrin-targeting LLG peptides and by the $\beta_2$ integrin blocking antibody 7E4 but not by antibodies to the $\beta_3$ integrins. It is notable that besides the LLG sequences von Willebrand factor contains I domains, similar to those present in the $\alpha$ subunits of the $\beta_2$ integrins. Thus, it is possible that there are intramolecular or intermolecular interactions between the LLG sequences and adjacent I-domains affecting the folding of the protein. If such interactions occur, they could in part explain the inactivity of the plasma form of von Willebrand factor. Our results suggest that leukocytes can bind to immobilized form of von Willebrand factor, such as present in vascular subendothelium or other surfaces, and these interactions could play a role in the initial phases of inflammation.

Interestingly, the LLGRPGEA sequence (SEQ ID NO: 7) of collagen IV $\alpha$ chain that we identified by a homology search shows a sequence similarity to the collagen-like peptide with a critical GFOGER motif (SEQ ID NO: 8) (O=hydroxyproline) which binds to $\alpha_2\beta_1$ integrin (Emsley et al, 2000). The glutamate residue of the peptide is seen to coordinate with a metal ion in a crystal structure of the complex between the collagen-like peptide and the $\alpha_2\beta_1$ integrin I-domain. It is possible that upon binding to an integrin, the glutamate located C-terminal to the LLG motif plays a similar metal ion-binding role both in ICAM-1 and collagen IV $\alpha$ chain.

The LLG-C4 nonapeptide is the shortest and most efficient peptide ligand yet developed for the $\beta_2$ integrins, and provides a lead structure for the development of $\beta_2$ integrin antagonists and potential anti-inflammatory agents. Because the $\beta_2$ integrins are expressed in blood cells and blood cell precursors in the bone marrow, these integrins should be readily accessible for targeting by circulating ligands. However, the $\beta_2$ integrins are known to exist in an inactive state and become activated only after physiologic stimuli such as by chemokines or through a contact with antigen-presenting cells. Therefore, it would be desirable and clinically useful to develop compounds binding preferentially to the cells bearing the activated integrins. The inventors found the LLG-C4 peptide to exhibit such properties as the immobilized peptide strongly bound cells only after their integrins were fully activated. The presence of LLG-like sequences in von Willebrand factor and collagens suggest a novel function for the proteins in mediating not only platelet but also leukocyte adhesion to the subendothelial matrix of a damaged blood vessel. Consequently, the inhibition of the binding of inflammatory cells and also leukemia cells to von Willebrand factor and type IV collagens by the peptides of the invention could be clinically useful. As ICAM-1 functions as the receptor for rhinoviruses which cause common colds, ICAM-1 mimicking peptides could also help the development of novel antiviral compounds (Casasnovas et al., 1998; Bella et al., 1998). The peptides of the invention could also be useful in the treatment of immune diseases, which include, but are not limited to, diabetes, rheumatoid arthritis, Crohn's disease, psoriasis, multiple sclerosis, and transplant rejection.

In a method for the therapeutic or prophylactic treatment of inflammatory diseases and human leukemias the therapeutically or prophylactically effective amount of the peptide of the invention to be administered to a subject in need of said treatment can vary depending on the condition, body weight, age, etc. of the subject in need of said treatment. For a mouse a suitable effective amount is for example 0.2 to 1 mg daily, administered intravenously or intraperitoneally, or about 10 mg during one week. In order to have an immediate effect on leukocytes, for bigger animals or human beings an effective amount in a single dose is for example 10 to 100 mg i.v.

The peptides of the present invention can also be used for identifying leukocyte cell types expressing $\beta$ integrins and may be valuable for typing inflammatory cells or diagnosing leukemias. Cells expressing an activated form of $\alpha_M\beta_2$ integrin, for example, can be isolated from blood or tissue by passing cell population through the surface of a column, and then eluting the cells with EDTA or a competitor peptide. This method may be particularly useful for isolating subsets of lymphocyte population expressing a panel of integrins.

The peptides of the present invention can also be used to promote the attachment of $\beta_2$ integrin expressing cells to a peptide surface or an artificial peptide matrix. Such an artificial matrix may work like a bone marrow or lymphatics and help in producing tissue transplants. On the other hand, the peptide in soluble form will prevent host reactions against a tissue transplant as the peptide inhibits $\beta_2$ integrin directed migration of macrophages and accompanying inflammatory reactions.

The following examples illustrate the invention without, however, limiting it in any way.

EXAMPLE 1

Phage Display

The $\alpha_M\beta_2$ integrin was purified by antibody affinity chromatography from buffy coats obtained from Finnish Red Cross Blood Transfusion Service as described previously (Li et al., 1995). Integrin diluted in Tris-buffered saline (TBS)/1 mM $MnCl_2$ was coated onto microtiter wells overnight at 4° C. using one µg per well in the first biopanning and 100, 10 and 1 ng in subsequent pannings. The wells were blocked with 5% BSA in TBS for 1 h at 22° C. and then washed five times with TBS. Biopanning was performed using $CX_7C$ and $CX_9C$ phage peptide libraries essentially as described (Koivunen et al., 1994). The construction of libraries was modified so that the single-stranded DNA encoding degenerate sequences was converted into a double-stranded form using 5 cycles of PCR with only the reverse primer and then 11 cycles with both the reverse and forward primer. A total of 6 µg of the double-stranded oligonucleotide was purified using QIAGEN PCR purification kit and ligated with 42 µg of the Fuse5 phage vector. The number of recombinants in the libraries was more than $10^9$. Phage binding, elution and subsequent amplification in E. coli were repeated five times, and after each panning bacterial colonies were picked up and stored in a 10 µl volume of TBS in microtiter wells at −20° C. For direct colony sequencing, one µl aliquots of the thawed samples were subjected to PCR with 10 pmol each of the forward primer 5' TAATACGACTCACTAT-AGGGCAAGCTGATAAACCGATACAATT 3' (SEQ ID NO: 9) and the reverse primer 5' CCCTCATAGTTAGCG-TAACGATCT 3' (SEQ ID NO: 10). The PCR conditions were 92° C. for 30 s, 60° C. for 30 s, and 72° C. for 60 s, and the cycle number was 35. One µl aliquot of the PCR reaction was taken for sequencing using 15 pmol of either one of the primers and analyzed on an ABI 310 apparatus (PE Applied Biosystems, Foster City, Calif.).

After the fifth round of selection, the $CX_7C$ library gave a 600-fold enrichment and $CX_9C$ a 1000-fold enrichment of phage bound to the integrin in comparison to background. Sequencing of the bound phage revealed altogether only seven different sequences, indicating selection of specific peptides by the integrin (Table 1). Four of them contained the LLG tripeptide motif. The two sequences most strongly enriched were CPCFLLGCC (SEQ ID NO: 3) (LLG-C4) and CWKLGSEEEC (SEQ ID NO: 11), each observed 15 times in the randomly selected clones, and these were the only clones remaining after searching for high affinity binders by using low integrin coating concentrations. Interestingly, LLG-C4 looks like a consensus binding sequence as all the peptides showed similarities to it with respect to the conservation of the proline, leucine, glycine, or cysteine residues.

TABLE 1

Seven phage sequences bound to the $\alpha_M\beta_2$ integrin (Mac-1) and their alignment with LLG-containing sequences present in cell adhesion proteins

|  | | | |
|---|---|---|---|
|  | CPCFLLGCC | (15) | (SEQ ID NO: 3) |
|  | CWKLLGSEEEC | (15) | (SEQ ID NO: 11) |
|  | CWHKDLLGC | (4) | (SEQ ID NO: 12) |
|  | CWSMELLGC |  | (SEQ ID NO: 13) |
|  | CPPDLFWYC | (4) | (SEQ ID NO: 14) |
|  | CPEDLYFFC | (3) | (SEQ ID NO: 15) |
|  | CPEDFIFFC |  | (SEQ ID NO: 16) |
| ICAM-1 | CDQPKLLGIETPL |  | (SEQ ID NO: 17) |
| von Willebrand Factor-A2 | TVGPGLLGVSTLG |  | (SEQ ID NO: 18) |
| von Willebrand Factor-D3 | GRYIILLGKALSV |  | (SEQ ID NO: 19) |
| type I collagen-α2 | PGPQGLLGAPGIL |  | (SEQ ID NO: 20) |
| type IV collagen-α4 | PGPPGLLGRPGEA |  | (SEQ ID NO: 21) |
| osteopontin | VICFCLLGITCAI |  | (SEQ ID NO: 22) |

The amino acids that are identical to the phage peptides are shown in bold. The ICAM-1 sequence is from the first Ig domain. The von Willebrand factor sequences are from A2 and D3 domains and the type I and IV collagen sequences from α chains. The osteopontin sequence includes residues no. 5–17. The number of isolated nucleotide sequences encoding each peptide is indicated in parenthesis.

Screening protein data bases indicated that the LLG tripeptide sequence is located on the first Ig domain of ICAM-1 just preceding the Glu-34 residue which is critical for ICAM-1 binding to the $\alpha_L\beta_2$ integrn (Staunton et al., 1990; Stanley and Hogg, 1998). The CWKLLGSEEEC (SEQ ID NO: 11) peptide showed the highest similarity, five out six consecutive residues being identical to the human ICAM-1 sequence (Table 1). The LLG tripeptide sequence is also contained in domains A2 and D3 of von Willebrand factor, in α chains of type I and IV collagen, and in osteopontin. None of these LLG-containing sequences, except that of ICAM-1, has been previously reported to contain potential cell attachment sites. von Willebrand factor (Savage et al., 1996) and osteopontin (Helluin et al., 2000) are protein ligands of the RGD-directed $\beta_3$ integrins but whether they can additionally bind to the $\beta_2$ integrins is not known. Interestingly, type I collagen has recently been shown to be a ligand of the $\alpha_x\beta_2$ integrin (Gamotel et al., 2000).

EXAMPLE 2

Integrin Binding Assays

Preparation of GST and Fc Fusion Proteins

The nucleotide sequence coding for LLG-C4 was PCR-amplified from phage DNA with the primers containing a BamH I (5' AGGCTCGAGGATCCTCGGC-CGACGGGGCT 3') (SEQ ID NO: 23) and an EcOR I site (5' AGGTCTAGAATTCGCCCCAGCGGCCCC 3'). (SEQ ID NO: 24). The PCR product was purified on an agarose gel, digested with the two restriction enzymes, and ligated into the PGEX-21K vector (Amersham Pharmacia Biotech, Uppsala, Sweden). Recombinants expressing LLG-C4-GST were verified by DNA sequencing. LLG-C4-GST was produced in E. coli strain BL 21 and purified by glutathione afity chromatography followed by dialysis. ICAM-1-Fc fusion protein containing the five ICAM-1 Ig domains was produced in CHO cells and purified by protein A affinity chromatography. Approximately 20 mg of LLG-C4-GST was produced, which was more than 95% pure as analyzed by SDS gel electrophoresis on the PhastSystem apparatus (Amersham Pharmacia).

Monoclonal Antibodies

Antibodies against the integrin $\beta_2$ subunit were 7E4, 11D3, 3F9, 1D10, and 2E7 as described previously (Nortamo et al., 1988). The anti $\alpha_L$ subunit antibodies were TS2/4 and MEM-83 (Monosan, Netherlands). The antibodies OKM1, OKM10 and MEM-170 were against the anti am subunit, and the antibody 3.9 against the $\alpha_X$ subunit (Li et al., 1993; Li et al., 1995). The $\alpha_{IIb}\beta_3$ integrin antibody P2 was purchased from Immunotech (Marseille, France), and the $\alpha_v\beta_3$ integrin antibody LM609 and the $\beta_1$ subunit antibody 6S6 from Chemicon (Temecula Calif.).

Integrin Binding Assays

Integrin was immunocaptured on microtiter wells that were coated with the $\alpha_M$ subunit antibodies OKM1 or MEM170, the $\alpha_x$ subunit antibody TS2/4 or non-specific IgG (Dako, Carpinteria, Calif.). The antibodies were coated at a concentration of 10 µg/ml in TBS overnight at 4° C. After saturation of the wells with 5% BSA, a 200 µl aliquot of the buffy coat lysate in 1% octylglucoside/1 mM $MnCl_2$/TBS was allowed to incubate for 2 h at 4° C. The wells were then washed five times with the octylglucoside-containing buffer. LLG-C4-GST or control GST was incubated at a concentration of 10 µg/ml in 25 mM octylglucoside TBS/1 mM $MnCl_2$ for an hour. Following washing of the wells, the bound GST was determined with anti-GST antibodies (Amersham Pharmacia), which were labeled with an $Eu^{3+}$-chelate according to the instructions of the manufacturer (Wallac, Turku, Finland). The $Eu^{3+}$-fluorescence was measured with a 1230 Arcus fluorometer (Wallac). For examination of the I-domain binding, we used the recombinant $\alpha_M$ I-domain expressed as a GST fusion protein in E. coli as described (Ueda et al., 1994). The fusion protein was purified by affinity chromatography on glutathione-coupled beads, and cleaved with thrombin to release the recombinant I-domain exhibiting a molecular weight of about 23 kDa. The I-domain was coated on microtiter wells at a concentration of 20 µg/ml, and the binding of LLG-C4-GST and GST was studied.

The LLG-C4-GST fusion protein, but not GST alone, was found to have potent activity and bound to the $\alpha_M\beta_2$ integrin in a divalent cation-sensitive manner like a typical integrin ligand. The cation-chelator EDTA inhibited the binding of LLG-C4-GST to the integrin, which was immunocaptured on microtiter wells with the $\alpha_M$ subunit antibody MEM170 or OKM1 (FIG. 1A). Similar EDTA-inhibitable binding of LLG-C4-GST was detected on the α integrin, which was captured with the TS2/4 antibody. LLG-C4-GST binding did not differ from GST control and was not inhibitable by EDTA, when a nonspecific IgG was used for immunocapture (not shown).

We also studied whether the peptide can directly interact with the I-domain of $\alpha_M\beta_2$ integrin, the known ligand-binding site. LLG-C4-GST, examined at the concentrations of 0.01–100 μg/ml, showed a concentration-dependent binding to isolated I-domain of the $\alpha_M$ subunit (FIG. 1B). GST at the same concentrations did not bind. The ability of the I-domain to bind LLG-C4-GST was dependent on the $Mn^{2+}$ cations added to the binding medium, and chelating $Mn^{2+}$ with EDTA blocked the binding (FIG. 1C). To show that the I-domain can also bind the LLG-C4 nonapeptide and not only the fusion protein, we synthesized the biscyclic LLG-C4 peptide. However, we had difficulties to prepare an active and water-soluble peptide, apparently because mixed disulfides easily formed during air-oxidation. One LLG-C4 (1) preparation was highly active and blocked the ability of the I-domain to bind the LLG-C4-GST (FIG. 1C). The same peptide was also active in cell culture experiments. Another preparation, LLG-C4 (2), was inactive apparently due to disadvantageous disulfide bonding and did not inhibit LLG-C4-GST binding to the I-domain.

EXAMPLE 3

Cell Culture and Adherence of Cell Lines to Nonapeptide Ligand

The Jurkat T cell leukemia (ATCC no. TIB-152), U-937 histiocytic lymphoma (no. CRL-1593.2), and K562 erytroleukemia (no. 45507) cell lines were maintained in RPMI 1640 medium supplemented with 2 mM glutamine, 10 mM HEPES, 1 mM sodium pyruvate, penicillin (100 U/ml), streptomycin (100 μg/ml) and 10% fetal calf serum (FCS). THP-1 monocytic leukemia cells (ATCC TIB-202) were cultured in the same medium containing in addition 0.05 mM 2-mercaptoethanol. The non-leukocytic cell lines Eahy926, HT1080, KS6717 and SKOV-3 were maintained as previously described (Koivunen et al., 1999). T cells were isolated from blood buffy coats by Ficoll-Hypaque centrifugation followed by passage through nylon wool columns (Valmu and Gahmberg, 1995). Wild-type mouse L929 cells and $\alpha_x\beta_2$ integrin-transfected L-cell line were obtained from Dr. Y. van Kooyk (University Hospital, Nijmegen, NL).

Cell Adhesion

Fibrinogen, fibronectin, von Wrlnebrand factor, type IV collagen, GST fusion proteins, Fc fusion proteins or synthetic peptides were coated on microtiter wells at a concentration of 2 μg in 50 μl TBS unless otherwise indicated. A recombinant von Willebrand factor and a capturing antibody to it kindly provided by Drs. J. J. Sixma and Ph. G. de Groot (University Medical Center Utrecht, the Netherlands) were also used. To prepare polymerized peptides, glutaraldehyde was added at a final concentration of 0.25%. The wells were saturated with 5% BSA and then washed five times with PBS. Prior to adhesion assays, cells were treated with 50 nM 40-Phorbol 12,13-dibutyrate or with 200 μM P1 peptide (Kotovuori et al., 1999) in serum-free medium for 30 min at room temperature to activate the integrins. Alternatively, cells were stimulated for 60 min at 37° C. with the phorbol ester (50 nM) and the C(1–8;3–9) and RGD-4C peptides each at a 2.5 μM concentration, after which the peptides were removed by washing with PBS/2.5 mM EDTA. Cells were incubated in the microtiter wells (100 000 cells per well) for 60 min at 37° C. in the absence or presence of competing peptides, antibodies or EDTA. Unbound cells were removed by gently washing with PBS and pressing the plate against paper towels. The bound cells were determined by an assay measuring cellular phosphatase activity. Briefly, 100 μl of 50 mM sodium acetate buffer, pH 5.0, containing 1% Triton X-100 and 6 mg/ml p-nitrophenyl phosphate was added per well and incubated for 1 h at 37° C. The reaction was stopped with 50 μl of 1 M NaOH. The absorbance at 405 nm was read on a microplate reader. Alternatively, the attached cells were stained with Crystal Violet essentially as described (Mould et al., 1995).

To study T cell binding to an endothelial cell monolayer, Eahy926 endothelial cells were plated on microtiter plates at a density of $5\times10^4$ cells per well and grown for three days. To stimulate the production of ICAM-1, the cells were further grown for 16 h in the presence of TNF-α at a concentration of 10 ng/ml. T cells ($1.5\times10^5$ per well) were allowed to bind to Eahy926 cells first for 30 min at 4° C., then 15 min at 37° C. The unbound T cells were removed by immersing the microtiter plate up side down in PBS. The bound cells were determined by the phosphatase assay.

Figure 2B:
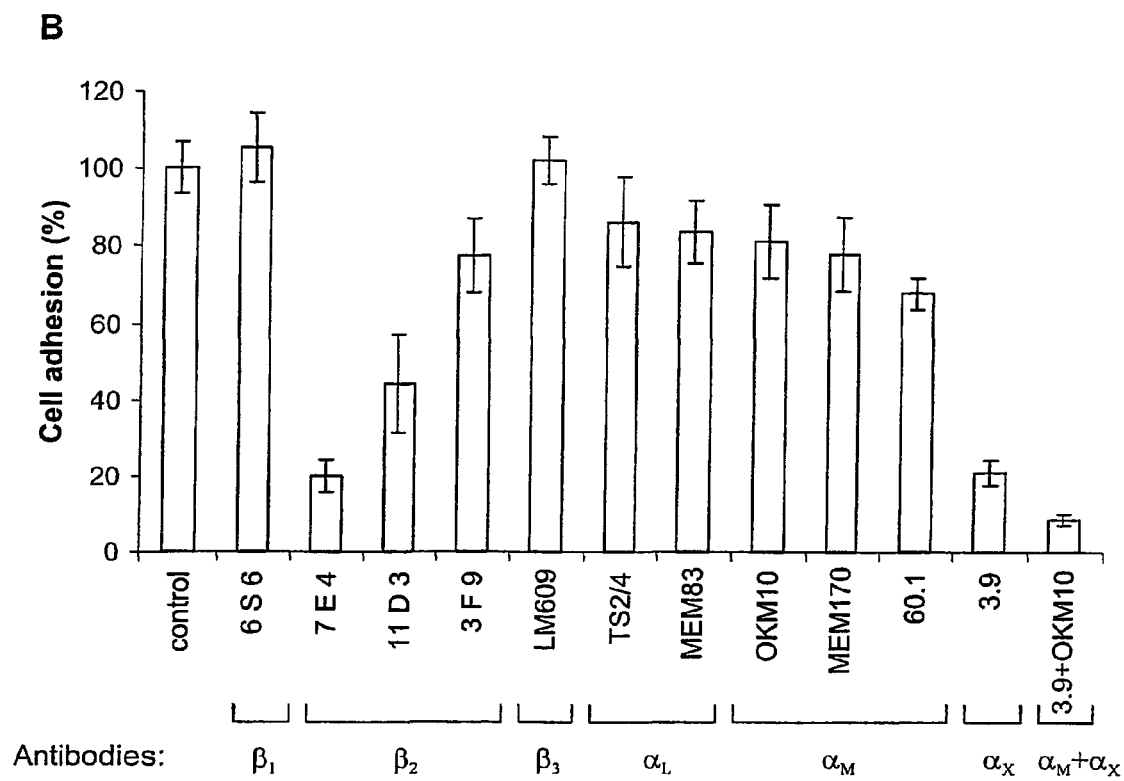
In FIG. 2(B), THP-1 cells were mixed with each antibody against the $\beta_1$, $\beta_2$, $\beta_3$, $\alpha_L$, $\alpha_M$, or $\alpha_X$ integrin subunit as indicated at a concentration of 50 µml. An aliquot of cells was then transferred to wells coated with LLG-C4-GST and incubated for 60 min at 37° C. Following washing the bound cells were determined by the phosphatase assay. The results are the mean % adhesion ±SD of 2–4 independent experiments each done in triplicate wells.

Phorbol ester-activated THP-1 monocytic leukemia cells efficiently bound to LLG-C4-GST but not to GST or peptide-GST controls (CLRSGRGC-GST, CPPWWSQC-GST) (SEQ ID NO: 25 AND 26) coated on microtiter wells (FIG. 2A). EDTA at a concentration of 2.5 mM completely abolished the binding on LLG-C4-GST. Screening with a panel of anti-integrin antibodies indicated that the cell adhesion on LLG-C4-GST was completely inhibited by the blocking antibody to the $\beta_2$ chain, 7E4 (FIG. 2B). Antibodies to the $\beta_1$ (6S6) and $\beta_3$ integrins (LM609, P2) had no effect Partial inhibition was obtained with the $\beta_2$ chain antibodies 11D3 and 3F9. The order of the potency of the three $\beta_2$ antibodies is the same as obtained previously in a granulocyte cell aggregation assay, 7E4 being the most active inhibitor of cell aggregation followed by 11D3 and 3F9 (Nortamo et al., 1988). The inventors also studied the $\beta_2$ chain antibodies 1D10, 2F3 and 2E7 that can activate the $\beta_2$-integrin mediated cell adhesion. In accordance, the three antibodies stimulated THP-1 cell adhesion on LLG-C4-GST (data not shown).

Studies with antibodies against the leukocyte integrin α subunits showed that a particularly strong inhibition on adhesion was obtained with the $\alpha_x$ subunit antibody 3.9. The $\alpha_M$ subunit antibodies OKM10, MEM170 and 60.1 were weakly inhibitory, whereas the $\alpha_L$-directed antibodies TS1/22 and TS2/4 had hardly any effect. THP-1 cells express $\alpha_x$ and $\alpha_M$ but only little $\alpha_L$, and the antibody inhibition profile is similar to that obtained for the inhibition of P1 peptide-stimulated THP-1 cell binding on fibrinogen (Li et al., 1995). Furthermore, the inventors found that the $\alpha_x$ antibody 3.9 and the $\alpha_M$ antibody OKM10 had a synergistic effect when added together, causing a complete inhibition of the cell adhesion.

EXAMPLE 4

Arrangement of the Cysteine Bonds on the Activity of LLG-C4

As the four cysteines present in the LLG-C4 can theoretically pair in different ways, we studied how the arrangement of the cysteine bonds affects the activity. For this purpose, we prepared synthetic peptides with different disulfide configurations. Peptides were synthesized using Fmoc-chemistry on an Applied Biosystems model 433A (Foster City, Calif.). Disulfides were formed by oxidation in 10 mM ammonium bicarbonate buffer (pH 9) overnight. Peptides were then purified by HPLC on an acetonitrile gradient. Generation of disulfides was confirmed by mass spectrometry analysis. The C(1–8;3–9) and C(1–9;3–8) peptides with the guided disulfide bridges were custom-made by Anaspec (San Jose, Calif.). The ACDCRGDCFCG (RGD-4C) peptide (SEQ ID NO: 27 (Koivunen et al., 1995) was obtained from Dr. E. Ruoslahti (Burnham Institute, San Diego, Calif.).

Figure 2C:
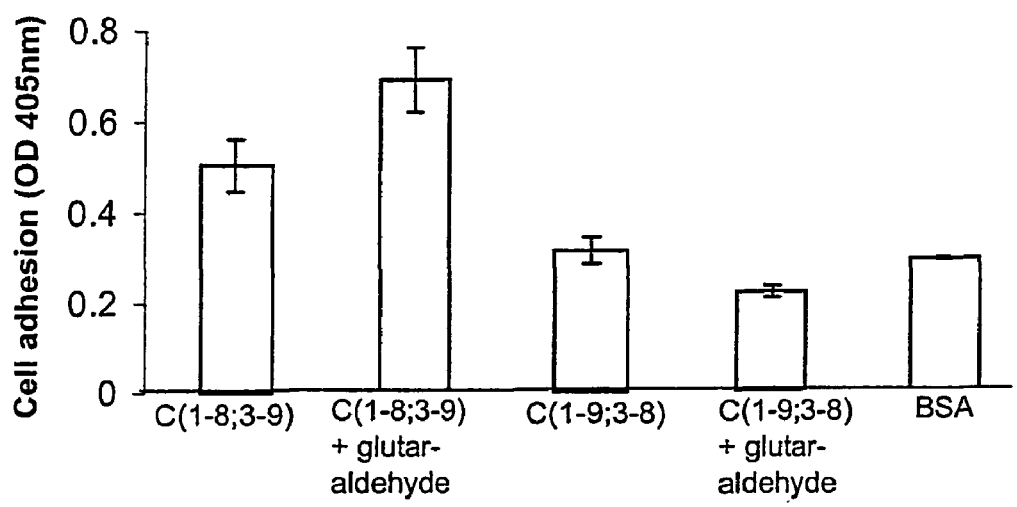
In FIG. 2(C), the C(1–8;3–9) and C(1–9;3–8) peptides were coated on microtiter wells by incubating overnight at a concentration of 40 µg/ml in TBS in the absence or presence of glutaraldehyde. Free binding sites on plastic were then blocked with 5% BSA. THP-1 cells (10 per well) were allowed to bind for 60 min at 37° C. After a wash with PBS, the bound cells were determined, and the results show the mean±SD of triplicate wells. The experiment was repeated twice.
Figure 2D:
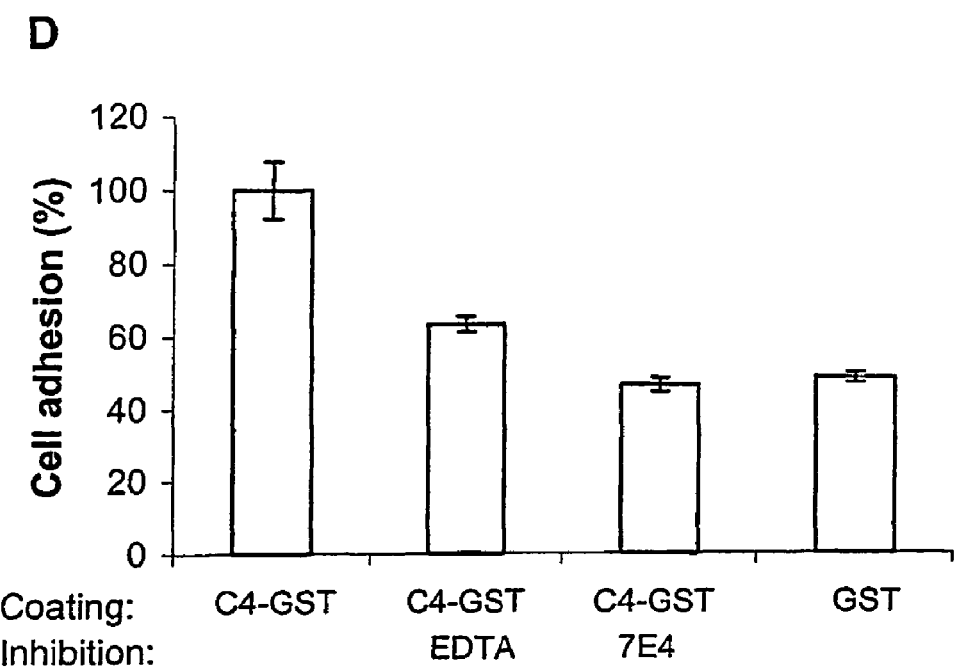
In FIG. 2(D), the $\alpha_X\beta_2$ integrin-transfected L cells were allowed to bind to LLG-C4-GST or GST. The 7E4 antibody and EDTA were used as competitors. The results mean % adhesion ±SD are representative of three experiments conducted in triplicate wells. The difference in the binding to LLG-C4-GST vs. GST is statistically significant (p=0.016).

The most active peptide C(1–8;3–9) was obtained by directing formation of one disulfide bond between the C1 and C8 cysteines, and a second disulfide bond between the C3 and C9 cysteines. The peptide C(1–9;3–8) had the disulfide bridges between the C1 and C9 cysteines, and between the C3 and C8 cysteines. Cells bound to the C(1–8;3–9) disulfide-containing peptide but failed to bind to the conformer with C(1–9;3–8) disulfides (FIG. 2C). Crosslinking of the C(1–8;3–9) peptide with glutaraldehyde further enhanced cell binding, apparently due to better coating of the multimeric peptide, whereas the same treatment of the C(1–9;3–8) peptide gave no cell binding. In general, the C(1–8;3–9) peptide specifically supported the binding of $\beta_2$ integrin-expressing cell lines such as $\beta_2$ integrin-transfected L cells and the leukocytic cell lines THP-1, U937 and Jurkat. The binding of $\alpha_X\beta_2$-transfected L cells to LLGC-C4-GST was inhibited by EDTA and the $\beta_2$ integrin blocking antibody 7E4 (FIG. 2D). Non-leukocytic cell lines L929, K562, SKOV-3, KS6717 and Eahy96, which do not express $\beta_2$ integrins, showed no binding to the peptide or GGL-C4-GCT, whether the cells were pretreated with phorbol ester or not (data not shown).

EXAMPLE 5

Blocking of $\beta_2$ Integrin-mediated Adhesion of Leukocyte Cell Lines by LLG-C4 Nonapeptide The ability of LLG-containing peptides to block leukocyte binding to adhesion proteins containing or lacking a LLG tripeptide sequence was examined. THP-1 cell adhesion on LLG-C4-GST was inhibited by the C(1–8;3–9) peptide with an $IC_{50}$ of 20 µM (FIG. 3A). The other conformer, C(1–9;3–8), was 20-fold less active than C(1–8; 3–9). To study whether the LLG tripeptide sequence is sufficient for recognition by the $\beta_2$ integrins, the inventors prepared the minimal CLLGC peptide (SEQ ID NO: 4) containing cysteines at the ends to induce a disulfide-constrained structure. In a control peptide the leucines were replaced by alanines. THP-1 cell adhesion experiments using the LLG-C4-GST substratum indicated that CAAGC (SEQ ID NO: 5) was a weak competitor of cell adhesion whereas CLLGC (SEQ ID NO: 4) readily inhibited cell adhesion at concentrations of 1 mM or higher, indicating a specific recognition of the LLG motif by the $\beta_2$ integrins (FIG. 3B).

Figure 4A:
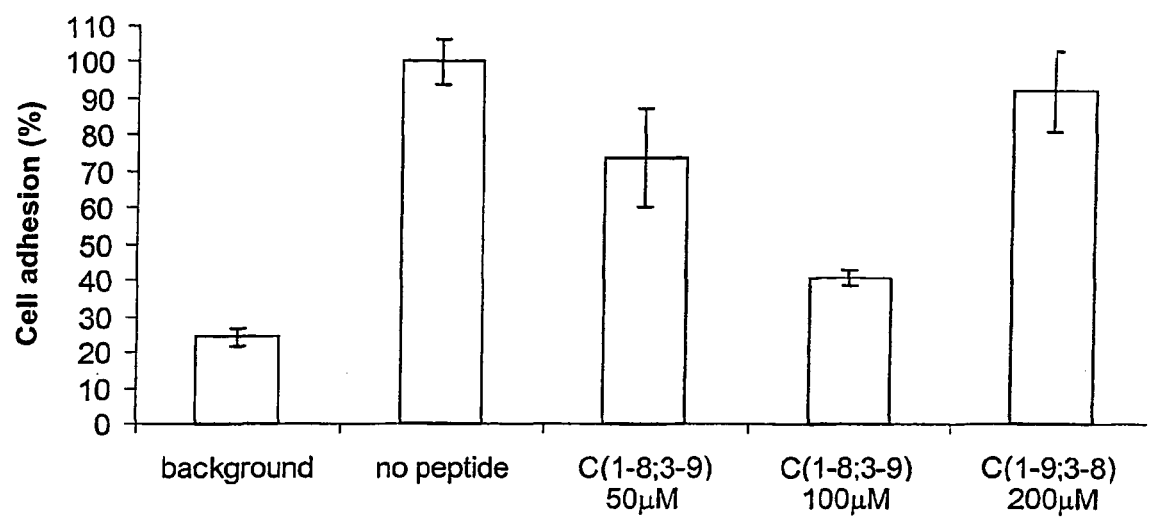
In FIG. 4(A), Jurkat cells were allowed to attach to immobilized ICAM-1-Fc in microtiter wells in the absence or presence of LLG-C4 peptides. Following a 45 min incubation, the unbound cells were removed by immersing the microtiter plate upside down on a decanter containing PBS, and the attached cells were stained with Crystal Violet. The results show % cell adhesion ±SD from two experiments each with triplicate or quadruplicate wells.
Figure 4B:
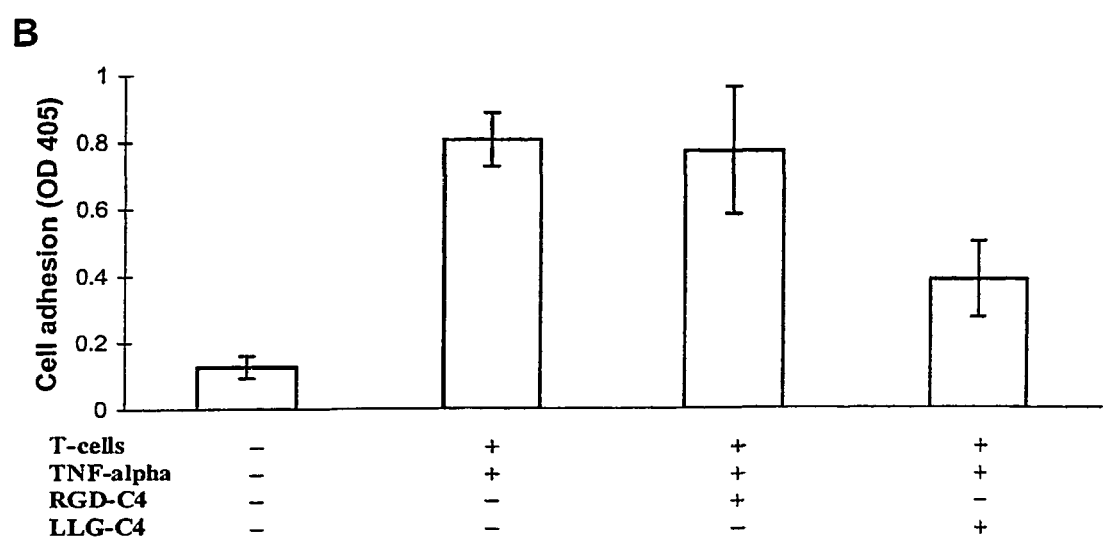
In FIG. 4(B), T cells were allowed to bind to TNF-α-stimulated Eahy endothelial cell monolayers that were grown on microtiter wells. LLG-C4 or RGD-4C was included at a concentration of 50 µM. After a 45 min incubation, the unbound cells were removed by immersing the microtiter plate in a PBS solution, and the bound T cells were determined by the phosphatase assay. The data are the mean ±SD of triplicate wells.

The ability of LLG-containing peptides to inhibit the $\alpha_L\beta_2$ integrin-mediated binding of Jurkat cells to ICAM-1-Fc recombinant protein, which includes the first Ig domain with the LLG sequence, was also examined. ICAM-1-Fc was directly coated or captured via protein A on microtiter wells. In both cases a concentration dependent inhibition by the C(1–8;3–9) peptide on Jurkat cell adhesion was found, and $IC_{50}$ was about 80 µM (FIG. 4A). The C(1–9;3–8) conformer was several fold less active and had hardly any effect. The C(1–8;3–9) peptide similarly inhibited the binding of freshly isolated T cells to cultured endothelial cells which were stimulated to express ICAM-1 by treatment with TNF-α (FIG. 4B). T cells did not bind to unstimulated endothelial cells. As a control, an RGD-containing peptide RGD-C4 had no effect on T cell binding to endothelial ICAM-1.

von Willebrand factor and type IV collagen are novel potential $\beta_2$ integrin ligands as they contain LLG-like peptide motifs. The inventors found that phorbol ester-activated THP-1 strongly bound to both proteins. The $\beta_2$ integrin antibody 7E4 blocked the THP-1 cell binding to von Willebrand factor (FIG. 5A) and was nearly as efficient inhibitor as the cation-chelator EDTA (data not shown). The $\beta_3$ integrin antibodies LM609 and P2 were without effect. The C(1–8;3–9) peptide was a potent inhibitor of THP-1 cell binding to von Willebrand factor. The peptide inhibited with an $IC_{50}$ of about 20 µM (FIG. 5B). In addition, the CLLGC (SEQ ID NO: 4) but not the CAAGC (SEQ ID NO: 5) peptide inhibited at a 500 µM concentration (data not shown). Similar C(1–8;3–9) peptide-mediated inhibition was observed on Jurkat cell binding to von Willebrand factor (not shown). THP-1 adhesion on type IV collagen was partially inhibited by the C(1–8;3–9) peptide. The $IC_{50}$ was about 200 µM. To further study the specificity of the LLG peptides, we examined THP-1 adhesion to fibronectin, a known ligand of several $\beta_1$ and $\beta_3$ integrins. The C(1–8;3–9) peptide showed no significant inhibition of fibronectin binding by THP-1 cells. The C(1–8;3–9) peptide also had no effect on $\beta_1$ and $\beta_3$ integin-mediated binding of HT1080 fibrosarcoma cells on fibronectin or fibrinogen (data not shown).

The C(1–8;3–9) peptide was capable of inhibiting THP-1 adhesion to fibrinogen, which does not contain a LLG sequence (FIG. 6A). The less potent C(1–9;3–8) conformer had no effect on fibrinogen binding. According to antibody inhibition experiments, the adherence of phorbol ester-stimulated THP-1 cells to fibrinogen is predominantly mediated via the $\alpha_M\beta_2$ and $\alpha_X\beta_2$ integrins as previously reported (Li et al., 1995). C(1–8;3–9) similarly inhibited the $\beta_2$ integrin-mediated fibrinogen binding to U937 monocytoid leukemia cells, which express the $\alpha_M\beta_2$ and $\alpha_X\beta_2$ integrins (data not shown). As RGD-dependent integrins can also mediate cell attachment on fibrinogen, the activity of C(1–8; 3–9) to that of RGD-4C, a potent ligand of several $\beta_1$ and $\beta_3$ integrins, was compared. THP-1 cells with low concentrations of the C(1–8;3–9) and RGD-4C peptides were pre-stimulated to fully activate both the $\beta_2$ and RGD-dependent integrins. After the peptide pre-stimulation, RGD-4C inhibited THP-1 cell adhesion on fibrinogen more effectively than C(1–8;3–9) (FIG. 6B). To study whether C(1–8,3–9) and RGD-4C target different integrins, the peptides were given together to cells. The effects of C(1–8;3–9) and RGD-4C were additive and the peptide combination blocked cell adhesion efficiently.

EXAMPLE 6

Cell Migration Assay

The in vitro migration of THP-1 cells was studied in closely physiological conditions containing 10% serum to not interfere with adhesive properties of cells. Both the upper and lower surfaces of 8 μm pore size Transwell filters were coated with fibrinogen, LLG-C4-GST, or GST at a concentration of 40 μg/ml overnight at 4° C. Free binding sites were blocked by incubation with 5% BSA/TBS. THP-1 cells ($5\times10^4$ in 100 μl) were plated on the upper compartment in 10% FCS-containing medium. The C(1–8;3–9) or C(1–9;3–8) peptide were included at a concentration of 200 μM. The lower compartment was filled with 750 μl of 10% FCS-containing medium. Following a culture for 18 h at 37° C. the filters were immersed in methanol for 15 min, in water for 10 s, and in 0.1% toluidine blue for 5 min. The filters were then washed 3–5 times with water until cell staining was clear. Cells were removed from the upper surface of the filter with a cotton swap, and cells migrated on the lower surface were counted microscopically. Student's t-test was used for statistical analysis.

Cells effectively migrated in the presence of 10% serum. The C(1–8;3–9) peptide at a concentration of 200 μM completely abolished the ability of the cells to traverse the filter and bind to its lower surface (FIG. 6C) (p=0.005, n=6). The C(1–9;3–8) conformer was less active than C(1–8;3–9) and inhibited only partially (p=0.01, n=6). The activity difference between the C(1–8;3–9) and C(1–9;3–8) peptides was significant (p=0.003). Cells did not spontaneously drop to the lower chamber through 8 μm-size pores of the filter. The majority of cells remained on the upper chamber after a one-day culture. In a reverse strategy where the filter was coated with LLG-C4, cell migration was strongly enhanced. Approximately 10-fold more cells migrated on the LLG-C4-GST substratum than on control GST substratum (FIG. 6D). Cell migration on LLG-C4-GST was also more efficient than on fibronectin or fibrinogen coatings. C(1–8;3–9) at the 200 μM concentration completely suppressed the cell migration on LLG-C4-GST (p=0.0026, n=6) (data not shown).

EXAMPLE 7

NMR Analysis of Peptides

C(1–8;3–9) and C(1–9;3–8) peptides were analyzed by NMR spectroscopy to determine whether there are differences in peptide conformations due to the directed arrangement of the disulfide bonds. For the determination, the C(1–8;3–9) peptide was dissolved in DMSO/H$_2$O (90/10) and C(1–9;3–8) in H$_2$O at the concentrations of 1–3 mM. The different solvents were due to the different solubility properties of the two peptides. Two-dimensional spectra, acquired with spectrometers operating at 600 and 800 Mhz $^1$H-frequency, allowed us to identity 114 nuclear Overhauser enhancements (nOes) for C(1–8;3–9) and 85 for C(1–9;3–8) peptide. Forty structures with no restraint violations above 0.2 Å were selected from families of 200 structures generated by simulated annealing (DYANA program).

Figure 7A:
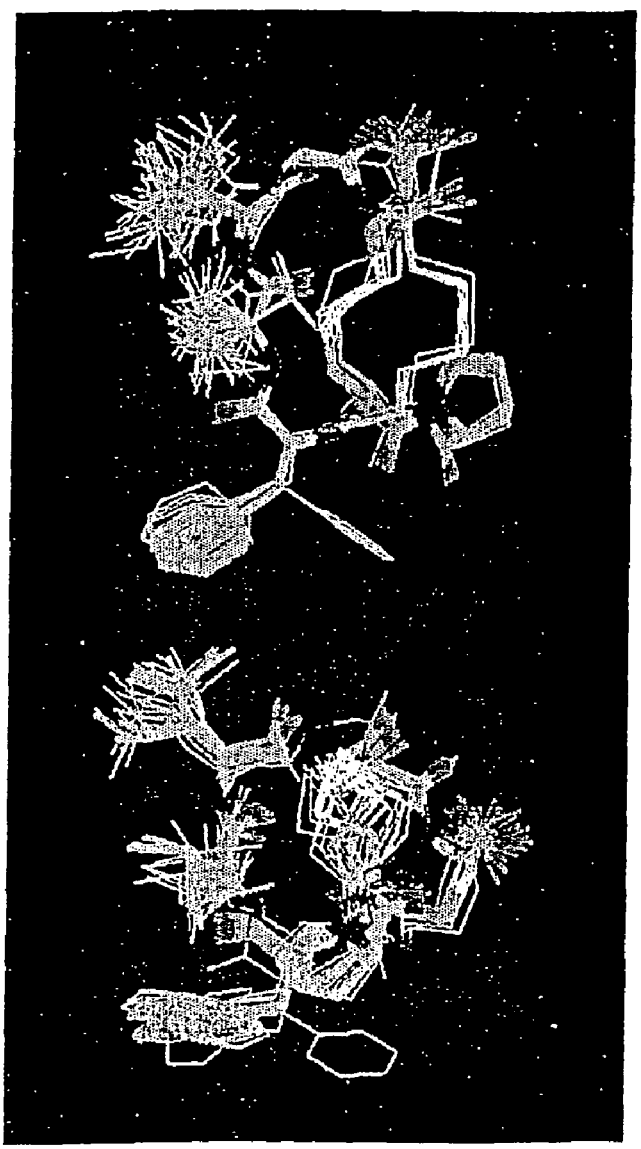
In FIG. 7(A), families of 40 conformations of C(1–8;3–9) (left) and C(1–9;3–8) (right) are shown. The heavy atoms of the disulfide-closed backbones are superimposed in each family and then the two families are translated apart for viewing.

The structure determinations of each nonapeptide resulted in well-defined backbone conformations. RMSD of the main chain atoms was 0.4±0.2 Å for C(1–8;3–9) and 0.3±0.2 Å for C(1–9;3–8) calculated from ensembles of 40 structures. For both peptides all main chain dihedrals ϕ and ψ are in the favorable and allowed regions of Ramachandran plot. There are only few nuclear Overhauser enhancements (nOes) to define the side chain orientation and therefore the side chain dihedrals of F4, L5 and L6, in particular, are dispersed (FIG. 7A).

The pairing of the disulphides in the two ways influenced the structure of the nonapeptide considerably. The "crossing arrangement of disulphides" of the C(1–8;3–9) peptide constrain the overall structure tighter than the "parallel arrangement of disulphides" of the C(1–9;3–8) peptide. This is reflected by the larger number of nOes observed for the C(1–8;3–9) peptide (114) than for the C(1–9;3–8) peptide (85). There is no bias towards shorter distance restraints in the C(1–8;3–9) peptide compared with those of the C(1–9;3–8) peptide. As a result of the two ways of pairing the disulphides there are interresidue nOes found exclusively in one of the structures, 37 in the C(1–8;3–9) peptide and 20 in the C(1–9;3–8) peptide.

Figure 7B:
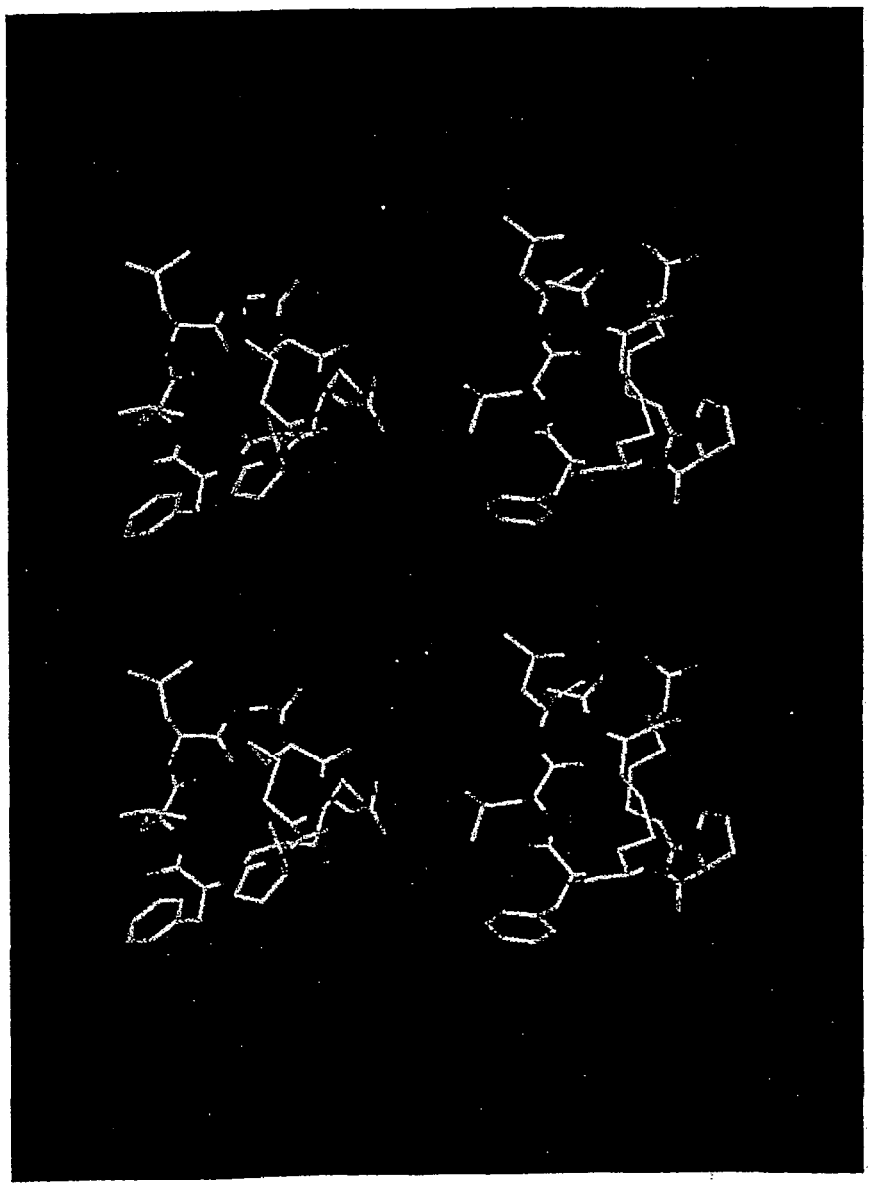
In FIG. 7(B), stereo views of representative solution structures C(1–8;3–9) (above) and C(1–9;3–8) (below) are shown For this presentation the two structures were initially superimposed on the main chain atoms of F4, L5 and L6, and then translated apart for viewing. In the C(1–8;3–9) peptide C1 pairs with C8 above and C3 with C9 below the cyclic structure. Likewise, in the C(1–9;3–8) peptide C1 pairs with C9 above and C3 with C8 below the ring.

The crossing arrangement of disulphides in the C(1–8;3–9) peptide is topologically more complicated than the parallel bridging in the C(1–9;3–8) peptide. In the short nonapeptide the adjacent disulphides with large van der Waals radii of sulphur atoms give rise to numerous steric restraints. The residue P2 also limits conformational freedom whereas G7 contributes to it. The impact of mere topology on the steric restraints is apparent from representative structures (FIG. 7B). The C(1–8;3–9) peptide is more compact than the C(1–9;3–8) peptide. Furthermore, there is a continuous hydrophobic surface patch composed of aliphatic groups of P2, F4 and L5 in the C(1–8;3–9) peptide. Overall, the disulphide bridges and the F4-L6 strand are buckled in the C(1–8;3–9) peptide whereas in the C(1–9;3–8) peptide they are extended. This likely accounts for the poorer water solubility of the C(1–8,3–9) peptide and may contribute to its higher activity.

Sequence Listing Free Text
For Seq. ID No. 2:
Variable aa, Xaa in position 2 can be any amino acid
Variable aa, Xaa in position 4 can be any amino acid

REFERENCES

Bella, J., Kolatkar, P. R. Manlor, C. W., Greve, J. M. and Rosmainn, M. G. (1998). The structure of the two amino-terminal domains of hubman ICAM-1 suggests how it functions as a rhinovins receptor and as an LFA-1 integrin ligand. Proc. Natl. Acad. Sci. USA 95, 4140–4145.

Casasnovas, J. M., Stehle, T., Liu, J., Wang, J., and Springer, T. A. (1998). A dimeric crystal structure for the N-terminal two domains of intercellular adhesion molecule-1. Proc. Natl. Acad. Sci. USA 95, 4134–4139.

Casasnovas, J. M., Pieroni, C., and Springer, T. A. (1999). Lymphocyte function-associated antigen-1 binding residues in intercellular adhesion molecule-2 (ICAM-2) and the integrin binding surface in the ICAM subfamily. Proc. Natl. Acad. Sci. USA 96, 3017–3022.

Emnsley, J., Knight, C. G., Famdale, R W., Barnes, M. J., and Liddington, R C. (2000). Structural basis of collagen recognition by integrin $\alpha_2\beta_1$. Cell 100, 47–56.

Feng, Y., Chung, D., Garrar, L., McEnroe, G., Lir, D., Scardina, J., McFadden, K, Guzzetta, A., Lam, A., Abraham, J., Liu, D., and Endemann, G. (1998). Peptides derived from the complementary-determining regions of anti-Mac-1 antibodies block intercellular adhesion molecule-1 interaction with Mac-1. J. Biol. Chem. 273, 5625–5630.

Fisher, K L., Lu, J., Riddle, L., Kim, K J., Presta, L. G., and Bodary, S. C. (1997). Identification of the binding site in intercellular adhesion molecule 1 for its receptor, leukocyte function-associated antigen 1. Mol. Biol. Cell. 8, 501–515.

Gahmberg, C. G., Tolvanen, M., and Kotovuori, P. (1997). Leukocyte adhesion. Structure and function of human leukocyte integrins and their cellular ligands. Eur. J. BiochenL 245, 215–232.

Garnotel, R., Rittié, L., Poitevin, S., Monboisse, J.-C., Nguyen, P., Potron, G., Maquart, F. -X, Randoux, A. and Gillery, P. (2000). Human blood monocytes interact with type I collagen through $\alpha_v\beta_3$ integrin (CD11c-CD18, gp150-95). J. Immunol. 164, 5928–5934.

Helluin, O., Chan, C., Vilaire, G., Mousa, S., DeGRado, W. F., and Bennett, J. S. (2000). The activation state of $\alpha_v\beta_3$ regulates platelet and lymphocyte adhesion to intact and thrombin-cleaved osteopontin. J. Biol. Chem. 275, 18337–18343.

Huang, C. and Springer, T. A. (1995). A binding interface on the I domain of lymphocyte function-associated antigen-1 (LFA-1) required for specific interaction with intercellular adhesion molecule-1 (ICAM-1). J. Biol. Chem. 270, 19008–19016.

Kallen, J., Welzenbach, K, Ramage, P., Geyl, D., Kriwacki R., Legge, G., Cottens, S., Weitz-Schmidt, G., and Hommel, U. (1999). Structural basis for LFA-1 inhibition upon lovastatin binding to the CD11a I-domain. J. Mol. Biol. 292, 1–9.

Kamata, T., Wright, R., and Takada, Y. (1995). Critical threonine and aspartic acid residues within the I domains of $\beta_2$ integrins for interactions of intercellular adhesion molecule-1 (ICAM-1) and C3bi. J. Biol. Chem. 270, 12531–12535.

Kelly, T. A., Jeanfavre, D. D., McNeil, D. W., Woska Jr., J. R., Reilly, P. L., Mainolfi, E. A., Kishirnoto, K. M., Nabozny, G. H., Zinter, R., Bormann, B. -J., and Rothlein, R (1999). A small molecule antagonist of LFA-1-mediated cell adhesion. J. Immunol. 163, 5173–5177.

Koivunen, E., Wang, B., and Ruoslahti, E. (1994). Isolation of a highly specific ligand for the $\alpha_5\beta_1$ integrin from a phage display library. J. Cell Biol. 124, 373–380.

Koivunen, E., Wang, B., and Ruoslahti, E. (1995). Phage libraries displaying cyclic peptides with different ring sizes: ligand specificities of the RGD-directed integrins. Bio/Technology 13, 265–270.

Koivunen, E., Arap, W., Valtanen, E., Rainisalo, A., Medina, O. P., Hejiddia, P., Kantor, C., Gahmberg, C. G., Salo, T., Konttinen, Y. T., Sorsa, T., Ruoslahti, E., and Pasqualini, R (1999). Tumor targeting with a selective gelatinase inhibitor. Nature Biotechnol. 17, 768–774.

Komoriya, A., Green, L. J., Mervic, M., Yamada, S. S., Yamada, K. M., and Humphries, M. J. (1991). The minimal essential sequence for a major cell type-specific adhesion site (CS1) within the alternatively spliced type III connecting segment domain of fibronectin is leucine-aspartic acid-valine. J. Biol. Chem. 266, 15075–15079.

Kotovuori, A., Pessa-Morikawa, T., Kotovuori, P., Nortatno, P., and Gahmberg, C. G. (1999). ICAM-2 and a peptide from its binding domain are efficient activators of leukocyte adhesion and integrin affinity. J. Immunol. 162, 6613–6620.

Kraft, S., Diefenbach, B., Mehta, R., Jonczyk, A., Luckenbach, G. A., and Goodman, S. L. (1999). Definition of an unexpected ligand recognition motif for $\alpha_v\beta_6$ integrin. J. Biol. Chem. 274, 1979–1985.

Lalancette, M., Aoudjit, F., Potworowski, E. F., and St-Pierre, Y. (2000). Resistance of ICAM-1 deficient mice to metastasis overcome by increased aggressiveness of lymphoma cells. Blood. 95, 314–319.

Li, R., Nortamo, P., Valmu L., Tolvanen, M., Huuskonen, J., Kantor, C., and Gahmberg, C. G. (1993). A peptide from ICAM-2 binds to the leukocyte integrin CD11a/CD18 and inhibits endothelial cell adhesion. J. Biol. Chem. 268, 17513–17518.

Li, R., Xie, J., Kantor, C., Koistinen, V., Altieri, D. C., Nortamo, P., and Gahmberg, C. G. (1995). A peptide derived from the intercellular adhesion molecule-2 regulates the avidity of the leukocyte integrins CD11b/CD18 and CD11c/CD18. J. Cell Biol. 129, 1143–1153.

Mould, A. P., Aidyama, S. K., and Humphries, M. J. (1995). Regulation of integrin $\alpha_5\beta_1$ -fibronectin interactions by divalent cations. Evidence for distinct classes of binding sites for $Mn^{2+}$, $Mg^{2+}$, and $Ca^{2+}$. J. Biol. Chem. 270, 26270–26277.

Nortamo, P., Patarroyo, M., Kantor, C., Suopanki, J. and Gahmberg, C. G. (1988). Immunological mapping of the human leukocyte adhesion glycoprotein gp90 (CD18) by monoclonal antibodies. Scand. J. Immunol. 28, 537–546.

Pierschbacher, M. D., and Ruoslahti, B. (1984). The cell attachment activity of fibronectin can be duplicated by small fragments of the molecule. Nature. 309, 30–33.

Ross, L., Hassman, F., and Molony, L. (1992). Inhibition of Molt-4-endothelial adherence by synthetic peptides from the sequence of ICAM-1. J. Biol. Chem. 267, 8537–8543.

Savage, B., Saldivar, E., and Ruggeri, Z. M. (1996). Initiation of platelet adhesion by arrest onto fibrinogen or translocation on von Willebrand factor. Cell. 84, 289–297.

Stanley, P., and Hogg, N. (1998). The I domain of integrin LFA-1 interacts with ICAM-1 domain 1 at residue Glu-34 but not Gln-73. Biol. Chem. 273, 3358–3362.

Staunton, D. B., Dustin, M. L., Erickson, H. P., and Springer, T. A. (1990). The arrangement of the immunoglobulin-like domains of ICAM-1 and the binding sites for LFA-1 and rhinovirus. Cell 61, 243–254.

Ueda, T., Rieu, P., Brayer, J., and Arnaout, M. A. (1994). Identification of the complement iC3b binding site in the $\beta_2$ integrin CR3 (CD11b/CD18). Proc. Natl. Acad. Sci. USA 91, 10680–10684.

Valmu, L., and Gabmberg, C. G. (1995). Treatment with ocadaic acid reveals strong threonine phosphorylation of CD18 after activation of CD11/CD18 leukocyte integrins with phorbol esters or CD3 antibodies. J. Immunol. 155, 1175–1183.

The invention claimed is:

1. An isolated peptide comprising the structure
CXCXLLGCC (SEQ ID NO: 2)
wherein X is any amino acid residue.

2. An isolated peptide comprising the structure
CPCFLLGCC (SEQ ID NO: 3).

3. The peptide according to claim 1 or 2, wherein said peptide is structurally constrained by two disulfide bonds.

4. The peptide according to claim 3, wherein said peptide contains one disulfide bond between the C1 and C8 cysteines, and a second disulfide bond between the C3 and C9 cysteines.

5. The peptide according to claim 3, wherein said peptide contains one disulfide bond between the C1 and C9 cysteines, and a second disulfide bond between the C3 and C8 cysteines.

6. A pharmaceutical composition comprising a peptide according to claim 1 in association with a pharmaceutically acceptable carrier.

7. The peptide according to claim 1, said peptide consisting of the structure
CXCXLLGCC (SEQ ID NO: 2)
wherein X is any amino acid residue.

8. The peptide according to claim 2, said peptide consisting of the structure
CPCFLLGCC (SEQ ID NO: 3).

* * * * *